United States Patent
Ino

(10) Patent No.: US 12,116,567 B2
(45) Date of Patent: Oct. 15, 2024

(54) METHOD FOR PRODUCING YEAST CONTAINING RICH-TASTE-IMPARTING SUBSTANCE AND METHOD FOR PRODUCING YEAST EXTRACT CONTAINING RICH-TASTE-IMPARTING SUBSTANCE

(71) Applicant: ASAHI GROUP FOODS, LTD., Tokyo (JP)

(72) Inventor: Tomokazu Ino, Tokyo (JP)

(73) Assignee: Asahi Group Foods, Ltd., Tokyo (JP)

( * ) Notice: Subject to any disclaimer, the term of this patent is extended or adjusted under 35 U.S.C. 154(b) by 627 days.

(21) Appl. No.: 17/309,448

(22) PCT Filed: Sep. 20, 2019

(86) PCT No.: PCT/JP2019/037028
§ 371 (c)(1),
(2) Date: May 27, 2021

(87) PCT Pub. No.: WO2020/115993
PCT Pub. Date: Jun. 11, 2020

(65) Prior Publication Data
US 2022/0033763 A1    Feb. 3, 2022

(30) Foreign Application Priority Data

Dec. 5, 2018 (JP) ................. 2018-228125

(51) Int. Cl.
| | |
|---|---|
| *C12N 1/18* | (2006.01) |
| *A23L 31/15* | (2016.01) |
| *C12P 1/02* | (2006.01) |
| *C12P 13/14* | (2006.01) |
| *C12P 21/02* | (2006.01) |

(52) U.S. Cl.
CPC ............... *C12N 1/18* (2013.01); *A23L 31/15* (2016.08); *C12P 1/02* (2013.01); *C12P 13/14* (2013.01); *C12P 21/02* (2013.01)

(58) Field of Classification Search
CPC ......... C12N 1/18; C12N 9/1022; A23L 31/15; C12P 1/02; C12P 13/14; C12P 21/02
See application file for complete search history.

(56) References Cited

U.S. PATENT DOCUMENTS

| | | |
|---|---|---|
| 2011/0262965 A1 | 10/2011 | Barrett et al. |
| 2013/0045305 A1 | 2/2013 | Nishiuchi et al. |
| 2013/0280381 A1 | 10/2013 | Nishiuchi et al. |
| 2016/0177323 A1 | 6/2016 | Morita et al. |

FOREIGN PATENT DOCUMENTS

| | | |
|---|---|---|
| JP | 06-261741 | 9/1994 |
| JP | 2007-252279 | 10/2007 |
| JP | 2010-029147 | 2/2010 |
| JP | 2011-160739 | 8/2011 |
| JP | 2013-524817 | 6/2013 |
| JP | 5857973 | 12/2015 |
| JP | 5954178 | 6/2016 |
| WO | 2015/005378 | 1/2015 |

OTHER PUBLICATIONS

Kingsbury J.M. et al., "Cytocidal amino acid starvation of *Saccharomyces cerevisiae* and Candida albicans acetolactate synthase (ilv2D) mutants is influenced by the carbon source and rapamycin", Microbiology, (2010), vol. 156, pp. 929-939. (Year: 2010).*
International Search Report issued Nov. 19, 2019 in PCT/JP2019/037028.
Written Opinion issued Nov. 19, 2019 in PCT/JP2019/037028.

* cited by examiner

*Primary Examiner* — Satyendra K Singh
(74) *Attorney, Agent, or Firm* — Grüneberg and Myers PLLC

(57) ABSTRACT

A method for producing a rich taste imparting substance-containing yeast, where the method includes: a yeast proliferating step of culturing a yeast that is modified to have a reduced acetolactate synthase activity in cells, and has isoleucine and valine requirements in a culture medium containing isoleucine and valine, to proliferate the yeast; and a rich taste imparting substance producing step of culturing the yeast with addition of valine to the culture medium when an isoleucine content in the culture medium is less than 0.2% by mass, to produce a rich taste imparting substance, wherein the rich taste imparting substance is at least one of γ-Glu-Abu and γ-Glu-Abu-Gly.

16 Claims, 10 Drawing Sheets

METHOD FOR PRODUCING YEAST CONTAINING RICH-TASTE-IMPARTING SUBSTANCE AND METHOD FOR PRODUCING YEAST EXTRACT CONTAINING RICH-TASTE-IMPARTING SUBSTANCE

CROSS-REFERENCE TO RELATED APPLICATIONS

This application is the National Stage entry under § 371 of International Application No. PCT/JP2019/037028, filed on Sep. 20, 2019, and which claims the benefit of Japanese Application No. 2018-228125, filed on Dec. 5, 2018. The content of each of these applications is hereby incorporated by reference in its entirety.

TECHNICAL FIELD

The present invention relates to a method for producing a rich taste imparting substance-containing yeast, which contains at least one of γ-Glu-Abu and γ-Glu-Abu-Gly, and a method for producing a rich taste imparting substance-containing yeast extract using the yeast.

BACKGROUND ART

Yeast extracts prepared from yeasts have a function of imparting, for is example, a savory taste and a rich taste to foods and are widely used in the food field as food additives such as seasonings. Because of the recent rise in the preference for naturalness, there is an increasing trend in the demand for yeast extracts.

Glutathione (hereinafter, may be referred to as "GSH"), which is a tripeptide formed of glutamic acid, cysteine, and glycine, is known as one of the components that impart a rich taste to foods.

Techniques proposed so far for increasing the GSH content in yeasts include a technique of producing a yeast mutant strain by deleting or mutating at least a part of a DOA1 gene and at least a part of a MET30 gene (for example, see PTL 1), and a technique of mutating yeast mutant strains containing a mutant MET30 gene to obtain two or more yeast mutant strains having a high glutathione content and hybridizing the obtained yeast mutant strains to obtain a yeast mutant strain having a higher GSH content (for example, see PTL 2).

γ-Glu-X and γ-Glu-X-Gly (where X represents an amino acid or an amino acid derivative except Cys and its derivatives) are also known as components that impart a rich taste to foods (for example, see PTL 3).

Techniques proposed so far for increasing the content of a component that imparts a rich taste include a technique of culturing a yeast in a culture medium in which Abu (L-2-amino butyric acid) and γ-Glu-Abu (L-γ-glutamyl-L-2 amino butyric acid) are added and preparing a yeast extract containing γ-Glu-Abu from the obtained fungal cells (for example, see PTL 4), and a technique of modifying cells to have a reduced acetolactate synthase activity and increasing the content of at least one selected from the group consisting of Abu, γ-Glu-Abu, and γ-Glu-Abu-Gly in the yeast cells (for example, see PTL 5).

As described above, various studies are made into techniques for increasing the content of a component that imparts a rich taste to foods. However, when, for example, industrial-scale production is taken into consideration, the content of at least one of γ-Glu-Abu and γ-Glu-Abu-Gly in yeasts or yeast extracts has not been enough yet, and urgent provision of a technique for more increasing the content is currently strongly demanded.

CITATION LIST

Patent Literature

PTL 1 Japanese Patent Application Laid-Open (JP-A) No. 2010-29147
PTL 2 JP-A No. 2011-160739
PTL 3 Japanese Patent (JP-B) No. 5857973
PTL 4 JP-B No. 5954178
PTL 5 International Publication No. WO 2015/005378

SUMMARY OF INVENTION

Technical Problem

The present invention aims for solving the various problems in the related art described above and achieving an object described below. That is, the present invention has an object to provide a method for producing a rich taste imparting substance-containing yeast, which highly contains at least one of γ-Glu-Abu and γ-Glu-Abu-Gly, and a method for producing a rich taste imparting substance-containing yeast extract.

Solution to Problem

As a result of conducting earnest studies to achieve the object described above, the present inventors have found it possible to remarkably increase the content of at least one of γ-Glu-Abu and γ-Glu-Abu-Gly in a yeast by proliferating a yeast that is modified to have a reduced acetolactate synthase activity in the cells and has isoleucine and valine requirements, and culturing the yeast with addition of valine to a culture medium when the isoleucine content in the culture medium is less than 0.2% by mass.

The present invention is based on the present inventors' finding described above, and means for solving the above problems are as follows.

<1> A method for producing a rich taste imparting substance-containing yeast, the method including:
   a yeast proliferating step of culturing a yeast that is modified to have a reduced acetolactate synthase activity in cells and has isoleucine and valine requirements in a culture medium containing isoleucine and valine, to proliferate the yeast; and
   a rich taste imparting substance producing step of culturing the yeast with addition of valine to the culture medium when an isoleucine content in the culture medium is less than 0.2% by mass, to produce a rich taste imparting substance,
   wherein the rich taste imparting substance is at least one of γ-Glu-Abu and γ-Glu-Abu-Gly.
<2> A method for producing a rich taste imparting substance-containing yeast extract, the method including
   preparing a yeast extract from the rich taste imparting substance-containing yeast obtained by the method for producing a rich taste imparting substance-containing yeast according to any one of <1> to <4>.

Advantageous Effects of Invention

The present invention can solve the various problems in the related art described above, achieve the object described above, and provide a method for producing a rich taste imparting substance-containing yeast, which highly contains at least one of γ-Glu-Abu and γ-Glu-Abu-Gly, and a method for producing a rich taste imparting substance-containing yeast extract.

Figure 1A:
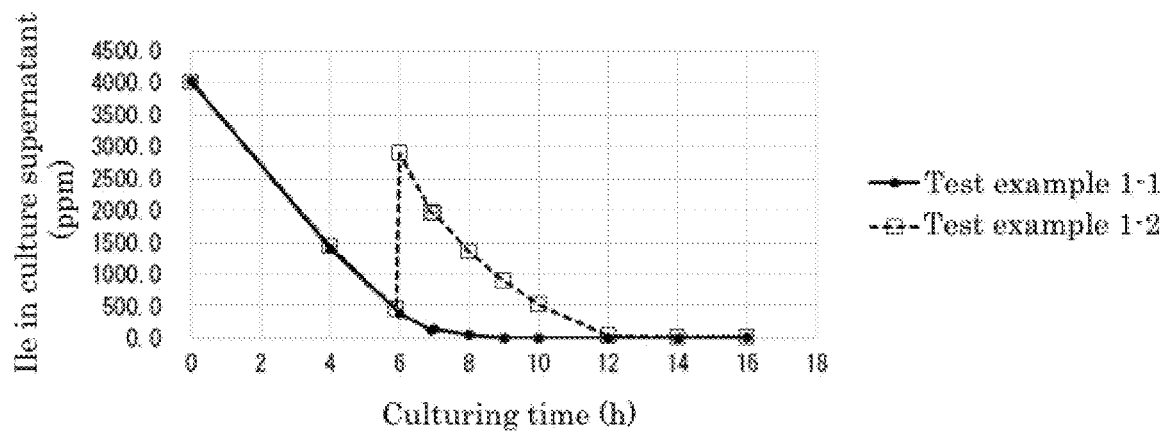
FIG. 1A is a graph plotting the measurements of isoleucine content in a culture supernatant during main culture in Test example 1.

DESCRIPTION OF EMBODIMENTS (Method for Producing Rich Taste Imparting Substance-Containing Yeast)

A method for producing a rich taste imparting substance-containing yeast of the present invention includes at least a proliferating step and a rich taste imparting substance producing step, and further includes other steps as needed.

The rich taste imparting substance of the present invention is at least one of γ-Glu-Abu and γ-Glu-Abu-Gly. In the present invention, Abu and Glu are L bodies.

<Proliferating Step>

The proliferating step is a step of culturing a yeast that is modified to have a reduced acetolactate synthase activity in cells and has isoleucine and valine requirements in a culture medium containing isoleucine and valine, to proliferate the yeast.

—Yeast—

The yeast is modified to have a reduced acetolactate synthase activity in cells, and has isoleucine and valine requirements.

The yeast may be a budding yeast or a fission yeast.

Examples of the budding yeast include yeasts belonging to the genus *Saccharomyces* such as *Saccharomyces cerevisiae*, the genus *Candida* such as *Candida utilis*, the genus *Pichia* such as *Pichia pastoris*, and the genus *Hansenula* such as *Hansenula polymorpha*.

Examples of the fission yeast include yeasts belonging to the genus *Schizosaccharomyces* such as *Schizosaccharomyces pombe*.

Among these yeasts, *Saccharomyces cerevisiae* and *Candida utilis* that are often used for producing yeast extracts are preferable.

The yeast may be a monoploid or may have ploidy higher than or equal to diploidy.

The yeast that is modified to have a reduced acetolactate synthase activity in cells and has isoleucine and valine requirements is known to highly contain at least one selected from the group consisting of Abu, γ-Glu-Abu, and γ-Glu-Abu-Gly in the yeast cells (see International Publication No. WO 2015/005378).

A yeast produced by, for example, modification or a commercially available yeast may be used as the yeast that is modified to have a reduced acetolactate synthase activity in cells and has isoleucine and valine requirements.

The acetolactate synthase is a protein (EC 2.2.1.6) that has an activity to catalyze a reaction to produce α-acetohydroxybutyric acid and $CO_2$ from pyruvic acid and α-ketobutyric acid (α-KB). This activity is also referred to as "acetolactate synthase activity". In the present invention, the acetolactate synthase may or may not have an activity to catalyze a reaction to produce acetolactic acid and $CO_2$ from two pyruvic acid molecules.

The method for modifying a yeast to have a reduced acetolactate synthase activity in cells and to have isoleucine and valine requirements is not particularly limited, and a known method may be appropriately selected. Examples of the method include the method described in International Publication No. WO 2015/005378.

Specifically, for example, the acetolactate synthase activity in cells is reduced and isoleucine and valine requirements is developed through destruction of an ILV2 gene encoding the subunit for the acetolactate synthase activity.

Information on the nucleotide sequence of the ILV2 gene is available from, for example, a public database. For example, the nucleotide sequence of the ILV2 gene of *Saccharomyces cerevisiae* is disclosed in *Saccharomyces* Genome Database (yeastgenome.org/).

The method for destroying the ILV2 gene is not particularly limited, and a known method may be appropriately selected.

It is possible to confirm that the acetolactate synthase activity is reduced, by, for example, preparing crude enzyme solutions from both of the yeast before modification and the yeast after modification and comparing the acetolactate synthase activities of the crude enzyme solutions. The acetolactate synthase activity can be measured by, for example, a known method (F. C. Stormer and H. E. Umbarger, Biochem. Biophys. Res. Commun., 17, 5, 587-592(1964)).

As needed, the yeast may have any other property than it is modified to have a reduced acetolactate synthase activity in cells and has isoleucine and valine requirements.

The any other property is not particularly limited and may be appropriately selected depending on the intended purpose so long as the effect of the present invention is not spoiled. It is preferable that the yeast have an enhanced ability to produce glutathione. It is more preferable that the yeast have threonine resistance.

The method for enhancing the glutathione producing ability of the yeast is not particularly limited and may be appropriately selected depending on the intended purpose. For example, it is possible to select a yeast that is modified to have a reduced acetolactate synthase activity in cells, has isoleucine and valine requirements, and has an enhanced ability to produce glutathione, by hybridizing a yeast that is modified to have an enhanced ability to produce glutathione and a yeast that is modified to have a reduced acetolactate synthase activity in cells and has isoleucine and valine requirements by a known method.

A yeast produced by, for example, modification or a commercially available yeast may be used as the yeast that is modified to have an enhanced ability to produce glutathione.

The method for modifying a yeast to have an enhanced ability to produce glutathione is not particularly limited, and a known method may be appropriately selected. Examples of the method include a method of deleting or mutating at least a part of a DOA1 gene and at least a part of a MET30 gene as described in JP-A No. 2010-29147 (JP-B No. 5496480), and a method of mutating yeast mutant strains containing a mutant MET30 gene to obtain two or more yeast mutant strains having a high glutathione content and hybridizing the obtained yeast mutant strains to obtain a yeast mutant strain having a higher glutathione content as described in JP-A No. 2011-160739 (JP-B No. 5667365).

It is possible to confirm that the glutathione producing ability is enhanced, by, for example, measuring the total glutathione amounts in the yeast before modification and the yeast after modification by a method of Titze et al. (Analytical Biochemistry, Vol. 27, p. 502, 1969) and comparing the total glutathione amounts.

The method for obtaining a yeast having threonine resistance is not particularly limited, and a known method may be appropriately selected. Examples of the method include a method of selecting a yeast grown in a culture medium in which threonine is added.

—Culture Medium—

The culture medium used in the proliferating step is not particularly limited and may be appropriately selected depending on the intended purpose so long as the culture medium contains at least isoleucine and valine and can proliferate the yeast.

The isoleucine content in the culture medium used in the proliferating step is not particularly limited so long as the yeast can proliferate, may be appropriately selected depending on, for example, the intended amount of the yeast, and is preferably from 0.01% by mass through 2.0% by mass and more preferably from 0.1% by mass through 1.0% by mass.

The valine content in the culture medium used in the proliferating step is not particularly limited so long as the yeast can proliferate, may be appropriately selected depending on, for example, the intended amount of the yeast, and is preferably from 0.01% by mass through 2.0% by mass and more preferably from 0.1% by mass through 1.0% by mass.

Other components than isoleucine and valine in the culture medium used in the proliferating step and the amounts of such other components are not particularly limited. Any components and any amounts that are used for culturing microorganisms such as yeasts may be appropriately selected.

For example, examples of carbon sources include glucose, sucrose, acetic acid, ethanol, molasses, and spent sulfite pulp liquor. One of these carbon sources may be used alone or two or more of these carbon sources may be used in combination.

Examples of nitrogen sources include ammonia, inorganic salts such as ammonium sulfate, ammonium chloride, and ammonium phosphate, and nitrogen-containing organic substances such as corn steep liquor, casein, yeast extracts, and peptone. One of these nitrogen sources may be used alone or two or more of these nitrogen sources may be used in combination.

Phosphoric acid components such as calcium superphosphate and ammonium phosphate, potassium components such as potassium chloride and potassium hydroxide, magnesium components such as magnesium sulfate and magnesium hydrochloride, inorganic salts of, for example, zinc, copper, manganese, and iron ions, and vitamins may also be added in the culture medium.

—Culturing—

The manner for culturing the yeast in the proliferating step is not particularly limited, and a common yeast culturing manner may be appropriately selected. Examples of the manner include batch culture, fed-batch culture, and continuous culture. Among these manners, fed-batch culture and continuous culture are preferable in terms of industrial-scale production.

The conditions for culturing the yeast in the proliferating step are not particularly limited, and common conditions for culturing yeasts may be appropriately selected.

For example, the temperature is preferably from 20° C. through 40° C. and more preferably from 25° C. through 35° C.

The pH is preferably from 3.5 through 7.5 and more preferably from 4.0 through 6.9.

It is preferable to perform the culturing under aerobic conditions, and it is more preferable to perform the culturing with ventilation or stirring. The volume of ventilation and the conditions for stirring are not particularly limited and may be appropriately selected considering, for example, the culturing capacity or time, and the initial fungal concentration. For example, ventilation may be performed by about from 0.2 V.V.M. (Volume per volume per minutes) through 2 V.V.M, and stirring may be performed at about from 50 rpm through 900 rpm.

The culturing time is not particularly limited and may be appropriately selected depending on the intended amount of the yeast.

The amount of the yeast in the culture after the proliferating step is not particularly limited and may be appropriately selected depending on the intended purpose. The amount of the yeast expressed as dry cell weight of yeast may be, for example, about from 0.5% through 6%.

The method for measuring the dry cell weight of yeast is not particularly limited, and a known method may be appropriately selected.

<Rich Taste Imparting Substance Producing Step>

The rich taste imparting substance producing step is a step of culturing the yeast with addition of valine to the culture medium when the isoleucine content in the culture medium is less than 0.2% by mass, to produce a rich taste imparting substance.

—Amount of Isoleucine in Culture Medium when Adding Valine—

The isoleucine content in the culture medium when adding valine to the culture medium in the rich taste imparting substance producing step is not particularly limited and may be appropriately selected depending on the intended purpose so long as the isoleucine content is less than 0.2% by mass. The isoleucine content is preferably 0.05% by mass or less, more preferably 0.02% by mass or less, and particularly preferably 0.01% by mass or less.

The method for measuring the amount of isoleucine in the culture medium is not particularly limited, and a known method may be appropriately selected. Examples of the method include the method described in the Examples section below.

—Amount of Valine in Culture Medium when Adding Valine—

The valine content in the culture medium when adding valine to the culture medium in the rich taste imparting substance producing step is not particularly limited, may be appropriately selected depending on the intended purpose, and is preferably 0.1% by mass or less, more preferably 0.05% by mass or less, and particularly preferably 0.01% by mass or less.

The method for measuring the amount of valine in the culture medium is not particularly limited, and a known method may be appropriately selected.

Examples of the method include the method described in the Examples section below.

—Amount of Valine Added to Culture Medium—

The amount of valine added to the culture medium in the rich taste imparting substance producing step is not particularly limited and may be appropriately selected depending on the intended purpose so long as the rich taste imparting substance can be produced. The amount (mass) of valine per addition is preferably 0.5% or greater, more preferably 1% or greater, and particularly preferably 2.5% or greater per dry cell weight of yeast. The amount of valine in the preferable range is advantageous because the amount of the rich taste imparting substance to be produced can be more increased.

The upper limit of the amount of valine added to the culture medium is not particularly limited and may be appropriately selected depending on the intended purpose so long as the effect of the present invention is not spoiled. For example, the upper limit of the amount of valine expressed as an amount per addition may be 5% per dry cell weight of yeast.

The number of times to add valine to the culture medium in the rich taste imparting substance producing step may be one, or two or greater.

—Amount of Threonine Added to Culture Medium—

It is preferable to further add threonine to the culture medium in the rich taste imparting substance producing step.

Threonine may be added to the culture medium at the same time as or a different time from when adding valine. It is preferable to add threonine at the same time as when adding valine because the amount of the rich taste imparting substance to be produced can be more increased.

The amount of threonine added to the culture medium in the rich taste imparting substance producing step is not particularly limited and may be appropriately selected depending on the intended purpose so long as the effect of the present invention is not spoiled. The amount (mass) of threonine per addition is preferably 0.5% or greater, more preferably 1% or greater, and particularly preferably 2.5% or greater per dry cell weight of yeast. The amount of threonine in the preferable range is advantageous because the amount of the rich taste imparting substance to be produced can be more increased.

The upper limit of the amount of threonine added to the culture medium is not particularly limited and may be appropriately selected depending on the intended purpose so long as the effect of the present invention is not spoiled. For example, the amount of threonine per addition may be 10% per dry cell weight of yeast.

The number of times to add threonine to the culture medium in the rich taste imparting substance producing step may be one, or two or greater.

—Culture Medium—

As the culture medium used in the rich taste imparting substance producing step, the same culture medium as used in the proliferating step except the amounts of isoleucine and valine, and as needed, threonine may be used.

—Culturing—

The manner for culturing the yeast and the conditions for culturing the yeast in the rich taste imparting substance producing step are not particularly limited, and a common yeast culturing manner may be appropriately selected. For example, the same manner as used in the proliferating step may be used.

—Rich Taste Imparting Substance—

The content of the rich taste imparting substance in the yeast obtained in the rich taste imparting substance producing step is not particularly limited and may be appropriately selected depending on the intended purpose. The content of the rich taste imparting substance expressed as the total amount (mass) of γ-Glu-Abu and γ-Glu-Abu-Gly is preferably 0.3% or greater, more preferably 0.6% or greater, yet more preferably 1.0% or greater, and particularly preferably 1.3% or greater per dry cell weight of yeast.

The upper limit of the content of the rich taste imparting substance in the yeast obtained in the rich taste imparting substance producing step is not particularly limited and may be appropriately selected depending on the intended purpose so long as the effect of the present invention is not spoiled. For example, the upper limit of the content of the rich taste imparting substance expressed as the total amount (mass) of γ-Glu-Abu and γ-Glu-Abu-Gly may be 5% per dry cell weight of yeast.

The ratio between the content of the γ-Glu-Abu and the content of the γ-Glu-Abu-Gly is not particularly limited and may be appropriately selected depending on the intended purpose.

The method for measuring the amount of the rich taste imparting substance in the yeast is not particularly limited, and a known method may be appropriately selected. Examples of the method include the method described in the Examples section below.

The yeast may contain other components that contribute to imparting a rich taste than γ-Glu-Abu and γ-Glu-Abu-Gly.

<Other Steps>

The other steps are not particularly limited and may be appropriately selected depending on the intended purpose so long as the effect of the present invention is not spoiled. Examples of the other steps include a preculturing step of preparing the yeast used in the proliferating step.

The method for culturing the yeast, the conditions for culturing the yeast, and the culture medium in the preculturing step are not particularly limited. Any culturing method, culturing conditions, and culture medium that are commonly used for culturing microorganisms such as yeasts may be appropriately selected depending on the intended purpose.

The culture of the yeast obtained in the rich taste imparting substance producing step may be dried, to obtain a dry yeast having a high rich taste imparting substance content.

The method for drying is not particularly limited. Any method that is commonly performed when preparing a dry yeast may be appropriately selected. Examples of the method include a freeze-drying method, a spray drying method, and a drum drying method.

The obtained dry yeast may be processed into a powdery state.

The method for producing a rich taste imparting substance-containing yeast of the present invention can produce a yeast that highly contains the rich taste imparting substance and can be applied to industrial-scale production.

(Method for Producing Rich Taste Imparting Substance-Containing Yeast Extract)

A method for producing a rich taste imparting substance-containing yeast extract of the present invention prepares a yeast extract from the rich taste imparting substance-containing yeast obtained by the method for producing a rich taste imparting substance-containing yeast of the present invention described above.

The method for preparing the yeast extract is not particularly limited. A common method for preparing a yeast extract may be appropriately selected. Examples of the method include an autolysis method of solubilizing yeast cells utilizing, for example, a proteolytic enzyme inherent in the cells, an enzymolysis method of solubilizing a yeast with addition of an enzyme preparation derived from a microorganism or a plant, a hot water extraction method of dipping fungal cells in hot water for a certain period of time to solubilize the fungal cells, an acidolysis or alkalinolysis method of solubilizing fungal cells with addition of various acids or alkalis, a freezing-thawing method of performing freezing and thawing fungal cells once or more to smash the fungal cells, and a physical smashing method of smashing fungal cells by a physical impact.

The physical impact is not particularly limited and may be appropriately selected depending on the intended purpose. Examples of the physical impact include ultrasonication, homogenization under a high pressure, and smashing by mixing with a solid such as glass beads.

—Rich Taste Imparting Substance—

The content of the rich taste imparting substance in the yeast extract is not particularly limited and may be appropriately selected depending on the intended purpose. The content of the rich taste imparting substance expressed as the total amount (mass) of γ-Glu-Abu and γ-Glu-Abu-Gly is preferably greater than 1%, more preferably 5% or greater, and particularly preferably 10% or greater per dry weight of yeast extract.

The upper limit of the content of the rich taste imparting substance in the yeast extract is not particularly limited and may be appropriately selected depending on the intended purpose so long as the effect of the present invention is not spoiled. For example, the upper limit of the content of the rich taste imparting substance expressed as the total amount (mass) of γ-Glu-Abu and γ-Glu-Abu-Gly may be 17% per dry weight of yeast extract.

The ratio between the content of the γ-Glu-Abu and the content of the γ-Glu-Abu-Gly is not particularly limited and may be appropriately selected depending on the intended purpose.

The method for measuring the amount of the rich taste imparting substance in the yeast extract is not particularly limited, and a known method may be appropriately selected. Examples of the method include a method of measuring the amount of the rich taste imparting substance in the same manner as the method for measuring the amount of the rich taste imparting substance in the yeast described above.

The yeast extract may contain other components that contribute to imparting a rich taste than γ-Glu-Abu and γ-Glu-Abu-Gly.

The method for producing a rich taste imparting substance-containing yeast extract of the present invention can produce a yeast extract that highly contains the rich taste imparting substance and can be applied to industrial-scale production.

Applications of the rich taste imparting substance-containing yeast and the rich taste imparting substance-containing yeast extract obtained by the producing methods of the present invention are not particularly limited and may be appropriately selected depending on the intended purpose. For example, the rich taste imparting substance-containing yeast and the rich taste imparting substance-containing yeast extract can be used for various foods and beverages, and supplements.

EXAMPLES

The present invention will be described below by way of Preparation examples and Test examples. However, the present invention should not be construed as being limited to these Preparation examples and Test examples.

Preparation Example 1: Preparation of Yeast

A yeast strain that was modified to have a reduced acetolactate synthase activity in cells, had isoleucine and valine requirements, had an enhanced ability to produce glutathione, and had threonine resistance was prepared in the manner described below.

<Parent Strain (Monoploid: Type a)>

An ILV2 mutant strain, strain NCYC868 (type a) (obtained from National Collection of Yeast Cultures) was used as a strain that was modified to have a reduced acetolactate synthase activity in cells and had isoleucine and valine requirements.

<Parent Strain (Monoploid: Type a)>

A monoploid (type α) was obtained by a routine method, using a *Saccharomyces cerevisiae* strain ABYC1588 strain (Deposit No. FERM BP-10924, a strain deposited with National Institute of Advanced Industrial Science and Technology Patent Microorganisms Depositary (Higashi 1-1-1, Tsukuba-shi, Ibaraki), deposited on Oct. 19, 2007), which is described in JP-A No. 2011-160739 (JP-B No. 5667365), as a strain modified to have an enhanced ability to produce glutathione.

<Selection-1>

The monoploid (type a) and the monoploid (type a) were conjugated by a routine method, and cultured in the manner described below.

—Preculture—

A loopful of a colony was inoculated into a 5 mL YPD culture medium and cultured at 30° C. overnight. The resultant was used as a preculture solution.

—Main Culture—

A molasses-urea culture medium having the composition described below was prepared in a 200 mL baffled Erlenmeyer flask. The whole amount of the preculture solution described above was inoculated into the molasses-urea culture medium and cultured at 30° C. at a stirring speed of 200 rpm for 48 hours.

| --Molasses-urea culture medium-- | |
|---|---|
| Molasses (total sugar equivalent) | 8.0% by mass |
| Urea | 0.3% by mass |
| Ammonium sulfate | 0.08% by mass |
| Diammonium hydrogen phosphate | 0.04% by mass |
| YNB w/o AAAS | 0.17% by mass |
| (obtained from Difco Laboratories, Inc.) | |
| Adenine sulfate | 0.005% by mass |
| L-lysine | 0.01% by mass |
| L-tyrosine | 0.01% by mass |
| L-isoleucine | 0.02% by mass |
| L-valine | 0.02% by mass |
| Glycine | 0.1% by mass |

The dry cell weight (hereinafter, may be referred to as "DCW") of the yeast after the main culture was measured by a routine method. The total glutathione amount (hereinafter, may be referred to as "GSH" content) in the yeast after the main culture was measured by a method of Titze et al. (Analytical Biochemistry, Vol. 27, p. 502, 1969).

Referring to the measured DCW and GSH content as indices, a plurality of excellent diploid strains were selected.

<Selection-2>

The diploid strains selected in <Selection-1> was subject to tetrad separation. The fungal cells obtained by the separation were applied to culture media described below, and only a strain (a strain having simultaneous requirements of isoleucine and valine) grown in an SD culture medium containing isoleucine and valine (iv) was isolated.

—Co-Culture Media—
  (i) an SD culture medium
  (ii) an SD culture medium containing isoleucine in an amount of 0.01% by mass
  (iii) an SD culture medium containing valine in an amount of 0.01% by mass
  (iv) an SD culture medium containing isoleucine in an amount of 0.01% by mass and valine in an amount of 0.01% by mass The isolated strain was subjected to preculture and main culture in the same culturing manners as described in <Selection-1>.

The dry cell weight of yeast after the culture was measured by a routine method. The contents of γ-Glu-Abu and γ-Glu-Abu-Gly, which were the rich taste imparting substances in the yeast after the culture, and the content of Abu, which was the precursor of γ-Glu-Abu and γ-Glu-Abu-Gly, were measured in the manner described below.

—Measurement of, for Example, Rich Taste Imparting Substances—

The measurement was performed by LC-MS/MS detection of peptides that were fluorescently derivatized with 6-aminoquinoryl-N-hydroxysuccinimidyl carbamate (AQC).

Specifically MILLQ water (2.5 µL), 5-sM internal standard substance solutions (3-methyl-His-d2 (obtained from Sigma-Aldrich Co.) and Gly-d2 (obtained from Sigma-Aldrich Co.), both labeled with stable isotopes) (5 su, and a boric acid buffer (an accompanying item of an ACCQ-FLUOR (registered trademark) reagent kit obtained from Nihon Waters K.K.) (30 sW were added to a sample (2.5 µL) diluted to an appropriate concentration or to a standard solution (2.5 µL) containing 1 µM of Abu, γ-Glu-Abu, and γ-Glu-Abu-Gly.

To the resultant mixture, an AQC reagent solution (prepared by dissolving a reagent powder of the reagent kit mentioned above in acetonitrile (1 mL)) (10 µL) was added. The resultant mixture was heated for 10 minutes at 55° C. and then a 0.1% formic acid aqueous solution (100 µL) was added to the resultant, to obtain an analysis sample.

Next, the analysis sample prepared in the manner described above was separated by reversed phase liquid chromatography described below, and then introduced into a mass spectrometer. The separation conditions were as follows.

—Separation Conditions—
  (1) HPLC: AGILENT 1200 SERIES
  (2) Separation column: UNISON UK-PHENYL (with an inner diameter of 2.0 mm, a length of 100 mm, and a particle diameter of 3 µm (obtained from Imtakt Corporation))
  (3) Column temperature: 40° C.
  (4) Mobile phase A: an aqueous solution obtained by adjusting a 25 mM formic acid aqueous solution to pH of 6.0 with ammonia water
  (5) Mobile phase B: methanol
  (6) Flow velocity: 0.25 mL/minute
  (7) Elution conditions: Elution was performed using a mixture liquid of the mobile phase A and the mobile phase B. The ratio of the mobile phase B to the mixture liquid was as follows: at 0 minutes (5%), from 0 minutes through 17 minutes (from 5% through 40%), from 17 minutes through 17.1 minutes (from 40% through 80%), from 17.1 minutes through 19 minutes (80%), from 19 minutes through 19.1 minutes (from 80% through 5%), and from 19.1 minutes through 27 minutes (5%).

Subsequently, the derivatized products of Abu, γ-Glu-Abu, and γ-Glu-Abu-Gly eluted under the separation conditions described above were introduced into the mass spectrometer, and the contents of the derivatized products were determined by mass chromatograph. The analysis conditions were as follows.

—Analysis Conditions—
(1) Mass spectrometer: AB SCIEX API3200 QTRAP
(2) Detection mode: Selected Ion Monitoring (positive ion mode)
(3) Selected ions: see Table 1 below

TABLE 1

| Derivatized product | First mass analyzer | Second mass analyzer |
|---|---|---|
| Abu | 274.2 | 171.1 |
| γ-Glu-Abu | 403.4 | 171.1 |
| γ-Glu-Abu-Gly | 460.4 | 171.1 |
| 3-methyl-His-d2 | 343.4 | 171.1 |
| Gly-d2 | 248 | 171.1 |

The contents of the derivatized products of Abu, γ-Glu-Abu, and γ-Glu-Abu-Gly were determined with analyzing software ANALYST VER 1.4.2 (obtained from AB Sciex Ptd. Ltd.). As the internal standard substances for determination of the contents, a derivatized product of 3-methyl-His-d2 was used for the derivatized product of Abu, and a derivatized product of Gly-d2 was used for the derivatized product of γ-Glu-Abu or γ-Glu-Abu-Gly, respectively.

Very rarely, an admixture peak may had been observed during determination of the content of γ-Glu-Abu, depending on the sample. In such a case, the content was determined using the 145.2 or 104.1 ion as the selected ion of the second mass analyzer.

Referring to the measured contents of the rich taste imparting substances and dry cell weight of yeast as indices, excellent monoploid strains were selected.

<Obtainment of Diploids>

The monoploid strains obtained in <Selection-2> were sorted into the type a and the type a. The sorted strains were hybridized by a routine method, to obtain a plurality of diploid strains.

<Selection-3>

The strains obtained in <Obtainment of diploids> were subjected to fed-batch culture in the manner described below, using a flask or a jar.

—Culture (Flask)—

The strains were subjected to preculture and main culture in the same culturing manners as described in <Selection-1>.

—Culture (Jar)—
—Preculture—

Two culture media having the composition described below were produced with a volume of 3,000 mL (with a jar fermenter obtained from B.E. Marubishi Co., Ltd.). The culture media were mixed, and sterilized in an autoclave at 121° C. for 15 minutes.

| [Culture media] | |
|---|---|
| Molasses (total sugar equivalent) | 8.0% by mass |
| Urea | 0.3% by mass |

| [Culture media] | |
|---|---|
| Ammonium sulfate | 0.08% by mass |
| Diammonium hydrogen phosphate | 0.04% by mass |
| Adenine sulfate | 0.005% by mass |
| L-lysine | 0.01% by mass |
| L-tyrosine | 0.01% by mass |
| L-isoleucine | 0.02% by mass |
| L-valine | 0.02% by mass |
| Glycine | 0.1% by mass |

A loopful of the strains obtained in <Obtainment of diploids> and grown on a YPD plate medium were inoculated into the culture medium for preculture having the composition described above, and cultured under the culturing conditions described below.

After the culturing was completed, the whole amount of the fungal cells were collected by centrifugation (3,000 g×5 minutes), and washed with the same amount of sterilized water. Subsequently, the fungal cells were collected again by centrifugation, suspended in sterilized water, and adjusted to a solid concentration of from 10% by mass through 20% by mass. The resultant was used as a precultured fungal cell solution.

[Culturing Conditions]
Culturing temperature: 30° C.
Shaking: 400 rpm
Culturing time: 24 hours
Volume of ventilation: 3 L/minute (1 V.V.M.)

—Main Culture—

The strains were cultured in a culture medium having the composition described below under the culturing conditions described below by fed-batch culture.

| [Culture medium] | |
|---|---|
| Precultured fungal cell solution | 150 mL |
| Water | 2,000 mL |
| Ammonium sulfate (97%) | 1.33 mL |
| Molasses (with a sugar content of 36%) | 6.7 mL |
| Diammonium hydrogen phosphate | 0.06% by mass |
| L-isoleucine | 0.4% by mass |
| L-valine | 0.35% by mass |

[Culturing Conditions]
Culturing temperature: 30° C.
Culturing condition: 18 hours
pH: controlled to a lower limit of 5.5 and an upper limit of 6.7 with 25% caustic soda or 47% sulfuric acid
Stirring: at from 600 rpm through 800 rpm
Fed-batch culture medium: Molasses (with a sugar content of 36%) from 870 mL through 1,000 mL
Ammonia water (10%) from 100 mL through 200 mL
Phosphoric acid (85%) from 5 g through 20 g The dry cell weight of yeast after the main culture was measured by a routine method. The contents of the rich taste imparting substances in the yeast after the main culture were measured in the same manner as the method described in <Selection-2>.

Referring to the measured contents of the rich taste imparting substances and dry cell weight of yeast as indices, excellent diploid strains (hereinafter, may be referred to as "K16 strains") were selected.

The K16 strains were strains modified to have a reduced acetolactate synthase activity in cells, having isoleucine and valine requirements, and having an enhanced ability to produce glutathione.

<Selection-4>

The K16 strains obtained in <Selection-3> were applied to a culture medium obtained by adding threonine (2% by mass) to a YPD culture medium, and cultured at 30° C. Two of the colonies grown (hereinafter, may be referred to as "K16-1 strains" and "K-16-2 strains") were obtained.

Each of the colonies was subjected to preculture and main culture in the same culturing manners as described in <Selection-1>.

The dry cell weight of yeasts after the main culture were measured by a routine method. The contents of, for example, the rich taste imparting substances in the yeasts after the main culture were measured in the same manner as the method described in <Selection-2>.

As a result, the contents of the rich taste imparting substances per dry cell weight of yeast were γ-Glu-Abu contents of 0.43% in the K16-1 strains and 0.52% in the K16-2 strains, and γ-Glu-Abu-Gly contents of 0.46% in the K16-1 strains and 0.70% in the K16-2 strains. The Abu contents per dry cell weight of yeast were 0.53% both in the K16-1 strains and the K16-2 strains.

The K16 strains obtained in <Selection-3> were also cultured in the same manner, and the dry cell weight of yeast and the contents of, for example, the rich taste imparting substances were measured. As a result, the contents of the rich taste imparting substances per dry cell weight of yeast were a γ-Glu-Abu content of 0.08% and a γ-Glu-Abu-Gly content of 0.10%. The Abu content per dry cell weight of yeast was 0.06%.

From the results described above, it was revealed that addition of threonine resistance to the yeast increased the contents of the rich taste imparting substances and also increased the content of the rich taste imparting substance precursor.

Test Example 1

The K16-2 strains obtained in Preparation example 1 were subjected to preculture and main culture in the same manners as in the case in which the jar was used in <Selection-3> in Preparation example 1, except that the cultures were performed under the conditions described in <Test example 1-1> and <Text example 1-2> below.

Test Example 1-1

During the main culture, valine (1,000 ppm) (2.9% per dry cell weight of yeast) was added to the culture medium after seven hours passed from the start of the main culture, and the main culture was continued.

The isoleucine content in the culture supernatant immediately before the addition of valine was 118 ppm (0.0118% by mass), and the valine content therein was 363 ppm (0.0363% by mass). The amount of the yeast in the culture medium immediately before the addition of valine, expressed as dry cell weight of yeast, was 3.45%.

Test Example 1-2

During the main culture, isoleucine (2,000 ppm) was added to the culture medium after six hours passed from the start of the main culture, valine (1,000 ppm) (2.9% per dry cell weight of yeast) was added to the culture medium after seven hours passed from the start of the main culture, and the main culture was continued.

The isoleucine content in the culture supernatant immediately before the addition of valine was 1,973 ppm (0.1973% by mass), and the valine content therein was 899 ppm (0.0899% by mass). The amount of the yeast in the culture medium immediately before the addition of valine, expressed as dry cell weight of yeast, was 3.36%.

<Measurement>

—Measurement of Isoleucine and Valine Contents in Culture Supernatant—

The isoleucine and valine contents in the culture supernatant at the start of the main culture, and after four hours, six hours, seven hours, eight hours, nine hours, ten hours, 12 hours, 14 hours, and 16 hours from the start of the main culture were measured in the manner described below.

Figure 1B:
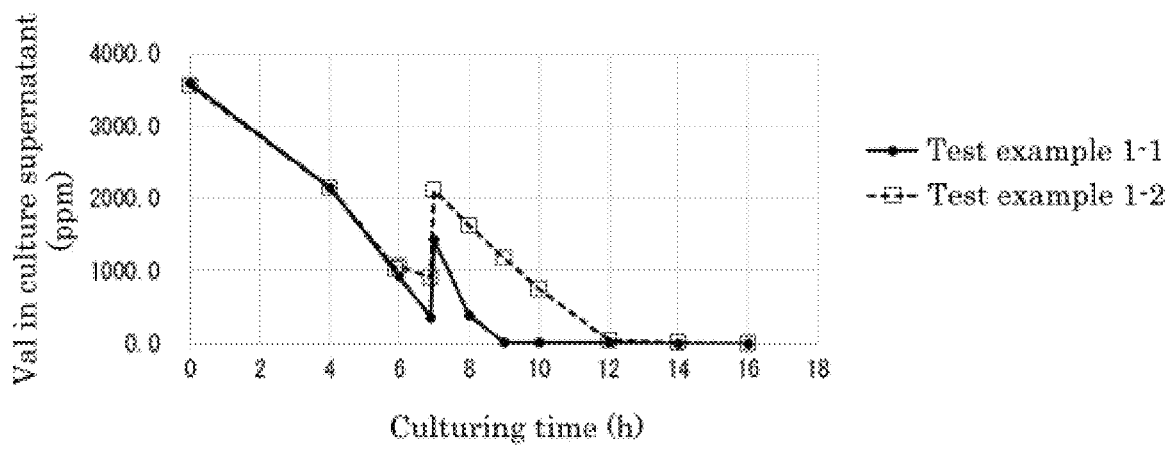
FIG. 1B is a graph plotting the measurements of valine content in a culture supernatant during main culture in Test example 1.

The results are plotted in FIG. 1A (isoleucine) and FIG. 1B (valine). In FIGS. 1A and 1B, "●, solid line" plots the results of Test example 1-1, and "□, dotted line" plots the results of Test example 1-2.

—Measurement of Isoleucine and Valine Contents—

The valine and isoleucine contents were measured by the Accutag Ultra (AccQ-Tag Ultra) labeling method using an "ACQUITY UPLC" analyzer obtained from Waters (USA).

—Measurement of Dry Cell Weight of Yeast—

The dry cell weight (hereinafter, may be referred to as "DCW") of the yeast at the start of the main culture, and after two hours, four hours, six hours, seven hours, eight hours, nine hours, ten hours, 11 hours, 12 hours, 13 hours, 14 hours, 16 hours, and 18 hours from the start of the main culture was measured by a routine method.

Figure 1C:
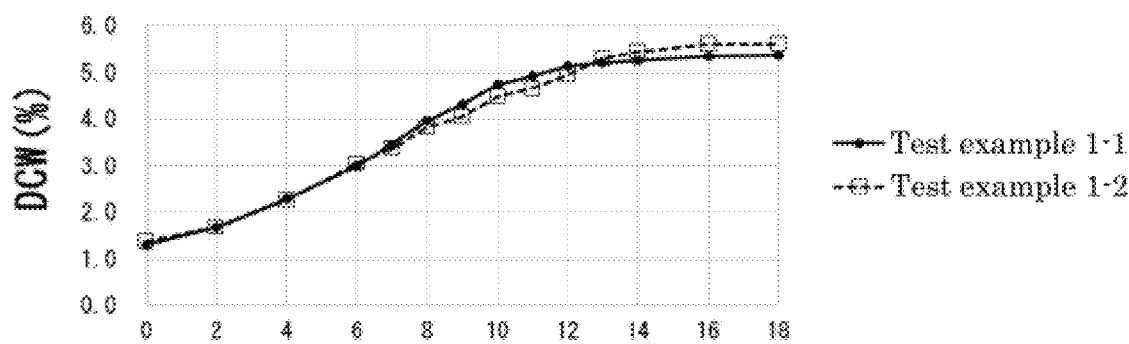
FIG. 1C is a graph plotting the measurements of dry cell weight of yeast during main culture in Test example 1.

The results are plotted in FIG. 1C. In FIG. 1C, "●, solid line" plots the results of Test example 1-1, and "□, dotted line" plots the results of Test example 1-2.

—Measurement of, for Example, Rich Taste Imparting Substances—

The yeast was collected after six hours, seven hours, eight hours, nine hours, ten hours, 11 hours, 12 hours, 13 hours, 14 hours, and 16 hours from the start of the main culture, and the contents (amounts per dry cell weight of yeast) of γ-Glu-Abu and γ-Glu-Abu-Gly, which were the rich taste imparting substances, and of Abu, which was the precursor of γ-Glu-Abu and γ-Glu-Abu-Gly, in the yeast were measured in the same manner as the method described in <Selection-2> in (Preparation example 1).

Figure 1D:
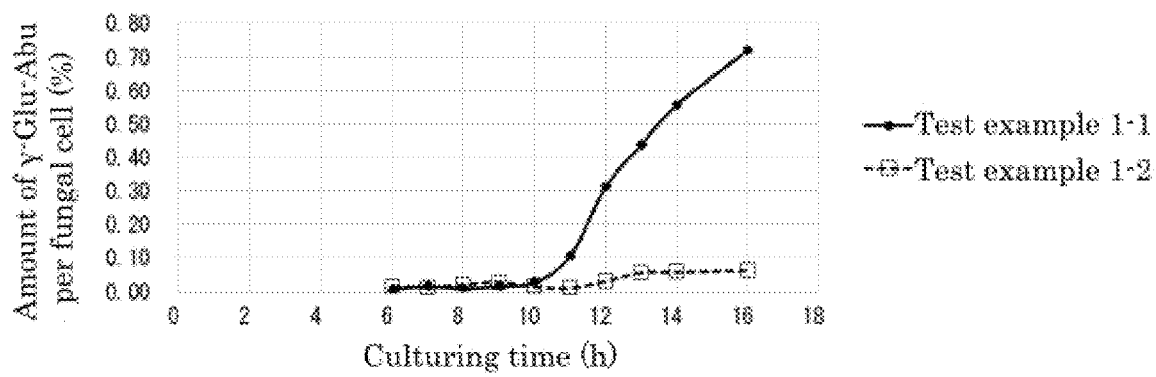
FIG. 1D is a graph plotting the measurements of γ-Glu-Abu amount per dry cell weight of yeast during main culture in Test example 1.
Figure 1E:
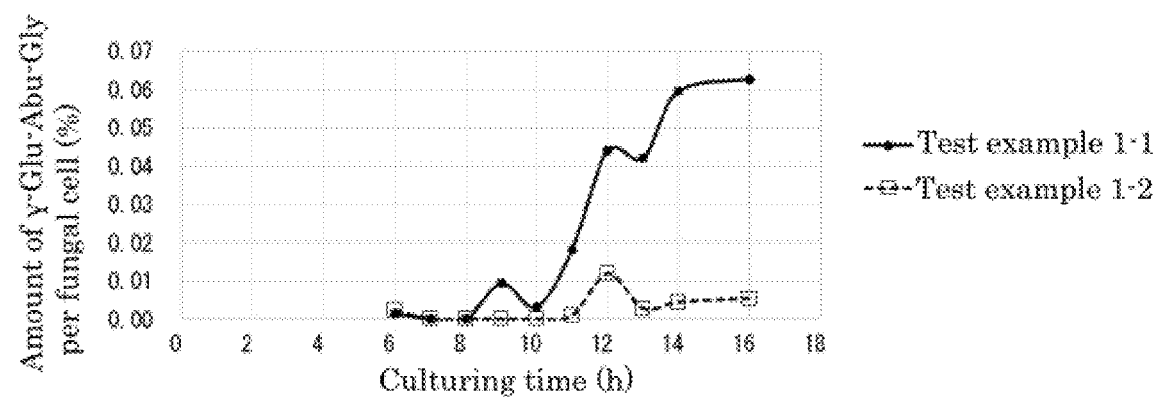
FIG. 1E is a graph plotting the measurements of γ-Glu-Abu-Gly amount per dry cell weight of yeast during main culture in Test example 1.
Figure 1F:
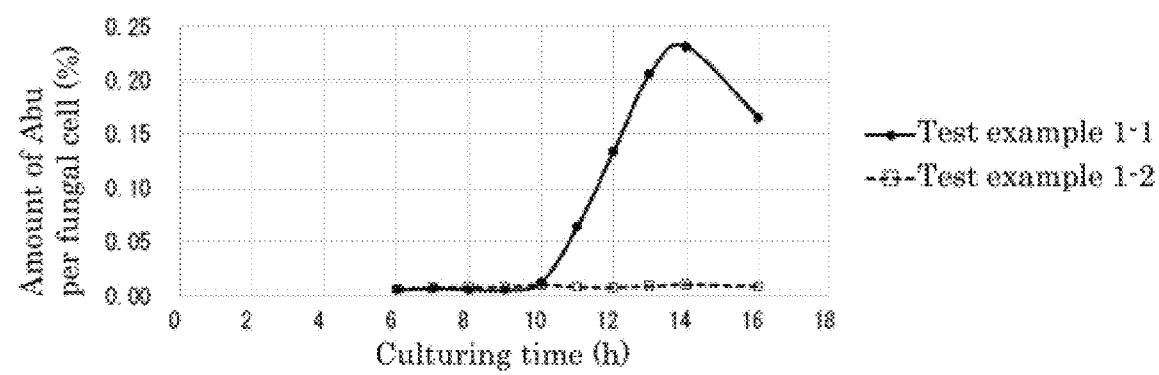
FIG. 1F is a graph plotting the measurements of Abu amount per dry cell weight of yeast during main culture in Test example 1.

The results are plotted in FIG. 1D (γ-Glu-Abu), FIG. 1E (γ-Glu-Abu-Gly), and FIG. 1F (Abu). In FIGS. 1D to 1F. "●, solid line" plots the results of Test example 1-1, and "□, dotted line" plots the results of Test example 1-2.

As plotted in FIGS. 1A to 1F, in Test example 1-1 in which the yeast was cultured with addition of valine when the isoleucine content in the culture supernatant was less than 0.2% by mass during the main culture, γ-Glu-Abu and γ-Glu-Abu-Gly, which were the rich taste imparting substances, were produced, and production of Abu, which was the precursor of the rich taste imparting substances, was also confirmed. On the other hand, in Test example 1-1 in which the yeast was cultured with addition of valine when the isoleucine content in the culture supernatant was 0.2% by mass, production of the rich taste imparting substances and the precursor thereof was extremely low.

Accordingly, it was confirmed that the method of the present invention was able to remarkably increase the amounts of the rich taste imparting substances produced.

Test Example 2

The K16-2 strains obtained in Preparation example 1 were subjected to preculture and main culture in the same manners as in the case in which the jar was used in <Selection-3> in Preparation example 1, except that the cultures were performed under the conditions described in <Test example 2-1> to <Text example 2-3> below.

Test Example 2-1

During the main culture, valine (1,000 ppm) (3.3% per dry cell weight of yeast) was added to the culture medium after six hours passed from the start of the main culture, and the main culture was continued.

The isoleucine content in the culture supernatant immediately before the addition of valine was 361 ppm (0.0361% by mass), and the valine content therein was 911 ppm (0.0911% by mass). The amount of the yeast in the culture medium immediately before the addition of valine, expressed as dry cell weight of yeast, was 2.98%.

Test Example 2-2

During the main culture, valine (1,000 ppm) (2.9% per dry cell weight of yeast) was added to the culture medium after seven hours passed from the start of the main culture, and the main culture was continued.

The isoleucine content in the culture supernatant immediately before the addition of valine was 118 ppm (0.0118% by mass), and the valine content therein was 363 ppm (0.0363% by mass). The amount of the yeast in the culture medium immediately before the addition of valine, expressed as dry cell weight of yeast, was 3.45%.

Test Example 2-3

During the main culture, valine (1,000 ppm) (2.5% per dry cell weight of yeast) was added to the culture medium after eight hours passed from the start of the main culture, and the main culture was continued.

The isoleucine content in the culture supernatant immediately before the addition of valine was 14.9 ppm (0.00149% by mass), and the valine content therein was 18.6 ppm (0.00186% by mass). The amount of the yeast in the culture medium immediately before the addition of valine, expressed as dry cell weight of yeast, was 4.01%.
<Measurement>
—Measurement of Isoleucine and Valine Contents in Culture Supernatant—

The isoleucine and valine contents in the culture supernatant at the start of the main culture, and after four hours, six hours, seven hours, eight hours, nine hours, ten hours, 12 hours, 14 hours, and 16 hours from the start of the main culture were measured in the same manner as in Test example 1.

Figure 2A:
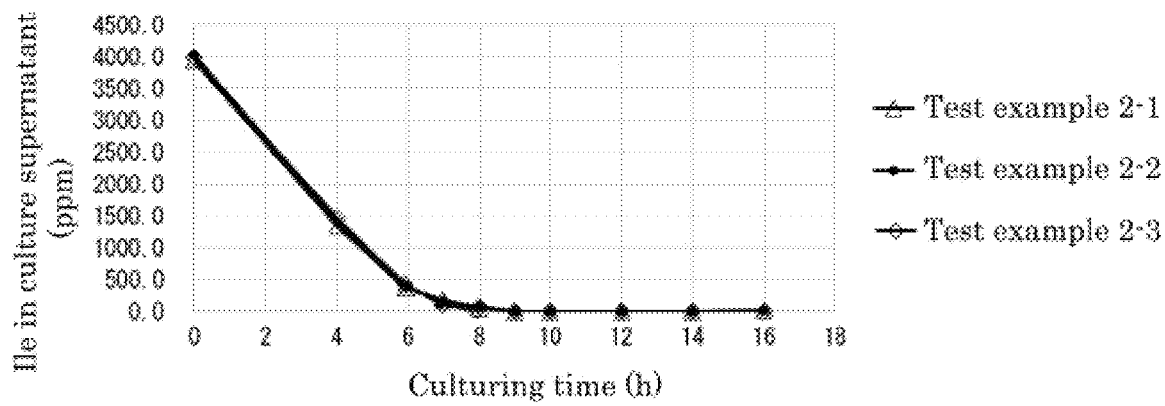
FIG. 2A is a graph plotting the measurements of isoleucine content in a culture supernatant during main culture in Test example 2.
Figure 2B:
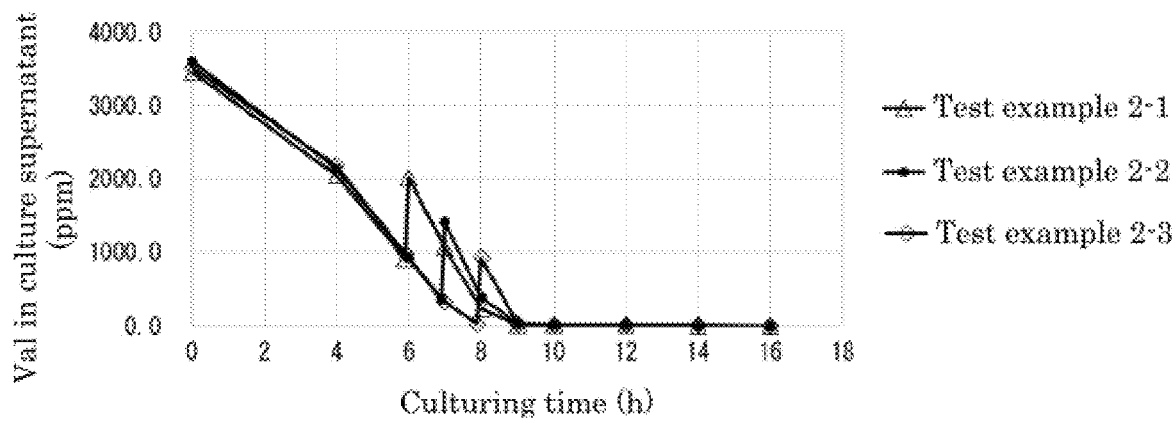
FIG. 2B is a graph plotting the measurements of valine content in a culture supernatant during main culture in Test example 2.

The results are plotted in FIG. 2A (isoleucine) and FIG. 2B (valine). In FIGS. 2A and 2B, "Δ, solid line" plots the results of Test example 2-1, "●, solid line" plots the results of Test example 2-2, and "◇, solid line" plots the results of Test example 2-3.
—Measurement of Dry Cell Weight of Yeast—

The dry cell weight of yeast at the start of the main culture, and after two hours, four hours, six hours, seven hours, eight hours, nine hours, ten hours, 11 hours, 12 hours, 13 hours, 14 hours, 16 hours, and 18 hours from the start of the main culture was measured in the same manner as in Test example 1.

Figure 2C:
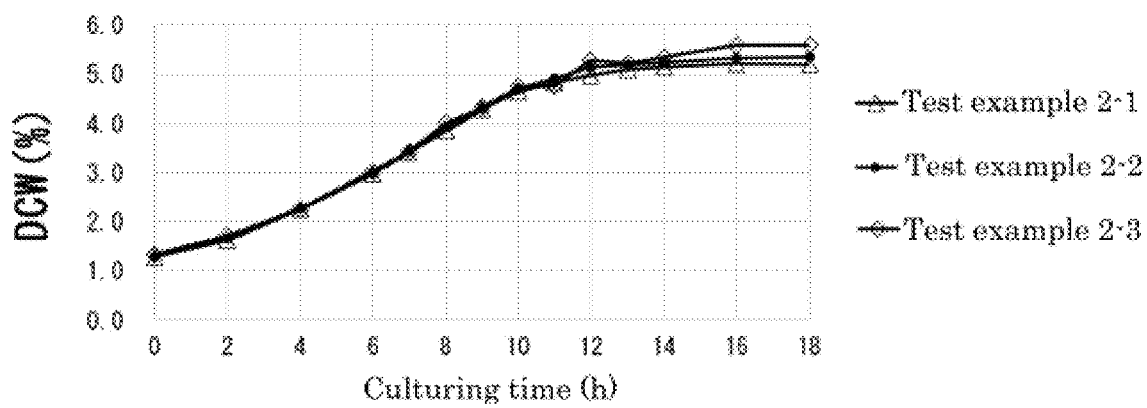
FIG. 2C is a graph plotting the measurements of dry cell weight of yeast during main culture in Test example 2.

The results are plotted in FIG. 2C. In FIG. 2C, "Δ, solid line" plots the results of Test example 2-1, "●, solid line" plots the results of Test example 2-2, and "◇, solid line" plots the results of Test example 2-3.

—Measurement of, for Example, Rich Taste Imparting Substances—

The yeast was collected after six hours, seven hours, eight hours, nine hours, ten hours, 11 hours, 12 hours, 13 hours, 14 hours, and 16 hours from the start of the main culture, and the contents (amounts per dry cell weight of yeast) of γ-Glu-Abu and γ-Glu-Abu-Gly, which were the rich taste imparting substances, and of Abu, which was the precursor of γ-Glu-Abu and γ-Glu-Abu-Gly in the yeast were measured in the same manner as the method described in <Selection-2> in (Preparation example 1).

Figure 2D:
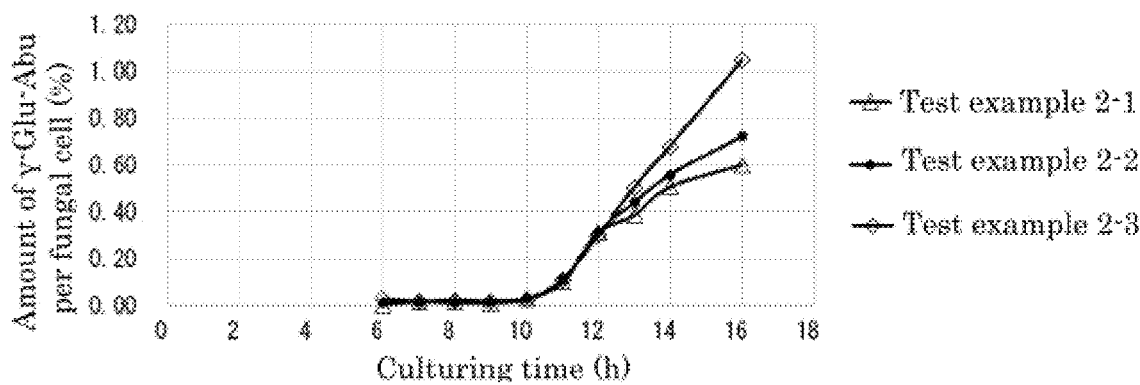
FIG. 2D is a graph plotting the measurements of γ-Glu-Abu amount per dry cell weight of yeast during main culture in Test example 2.
Figure 2E:
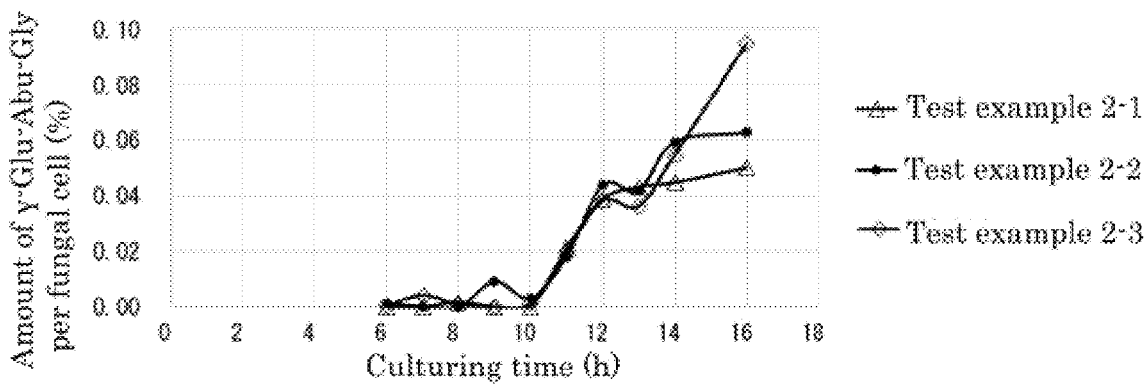
FIG. 2E is graph plotting the measurements of γ-Glu-Abu-Gly amount per dry cell weight of yeast during main culture in Test example 2.
Figure 2F:
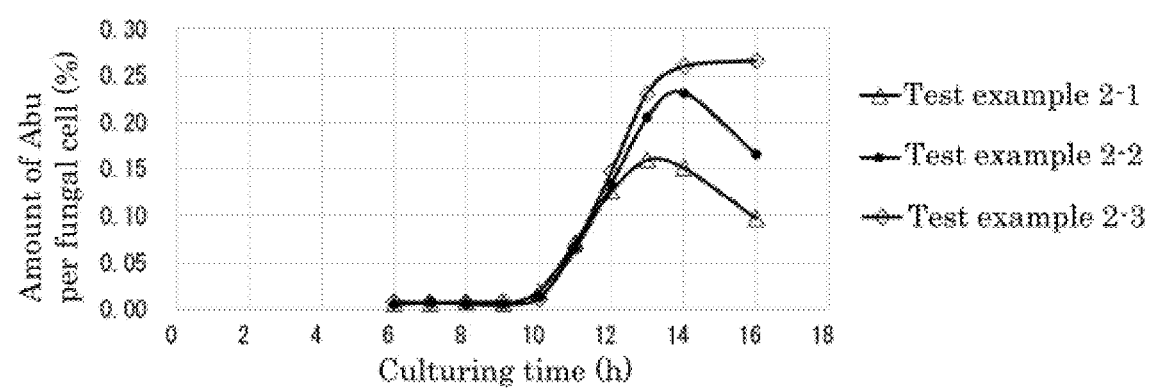
FIG. 2F is a graph plotting the measurements of Abu amount per dry cell weight of yeast during main culture in Test example 2.

The results are plotted in FIG. 2D (γ-Glu-Abu), FIG. 2E (γ-Glu-Abu-Gly), and FIG. 2F (Abu). In FIGS. 2D to 2F. "Δ, solid line" plots the results of Test example 2-1, "●, solid line" plots the results of Test example 2-2, and "◇, solid line" plots the results of Test example 2-3.

As plotted in FIGS. 2A to 2F, the amounts of the rich taste imparting substances and the precursor thereof produced were greater as the isoleucine and valine contents in the culture supernatant when adding valine during the main culture were lower.

Test Example 3

The K16-2 strains obtained in Preparation example 1 were subjected to preculture and main culture in the same manners as in the case in which the jar was used in <Selection-3> in Preparation example 1, except that the cultures were performed under the conditions described in <Test example 3-1> and <Text example 3-2> below.

Test Example 3-1

During the main culture, valine (1,000 ppm) (2.5% per dry cell weight of yeast) was added to the culture medium after eight hours passed from the start of the main culture, and the main culture was continued.

The isoleucine content in the culture supernatant immediately before the addition of valine was 14.9 ppm (0.00149% by mass), and the valine content therein was 18.6 ppm (0.00186% by mass). The amount of the yeast in the culture medium immediately before the addition of valine, expressed as dry cell weight of yeast, was 4.01%.

Test Example 3-2

During the main culture, valine (1,000 ppm) (2.6% per dry cell weight of yeast) and threonine (2,000 ppm) (5.2% per dry cell weight of yeast) were added to the culture medium after eight hours passed from the start of the main culture, and the main culture was continued.

The isoleucine content in the culture supernatant immediately before the addition of valine and threonine was 14.5 ppm (0.00145% by mass), and the valine content therein was 18.3 ppm (0.00183% by mass). The amount of the yeast in the culture medium immediately before the addition of valine, expressed as dry cell weight of yeast, was 3.86%.
<Measurement>
—Measurement of Isoleucine and Valine Contents in Culture Supernatant—

The isoleucine and valine contents in the culture supernatant at the start of the main culture, and after four hours, six hours, seven hours, eight hours, nine hours, ten hours, 12 hours, 14 hours, and 16 hours from the start of the main culture were measured in the same manner as in Test example 1.

Figure 3A:
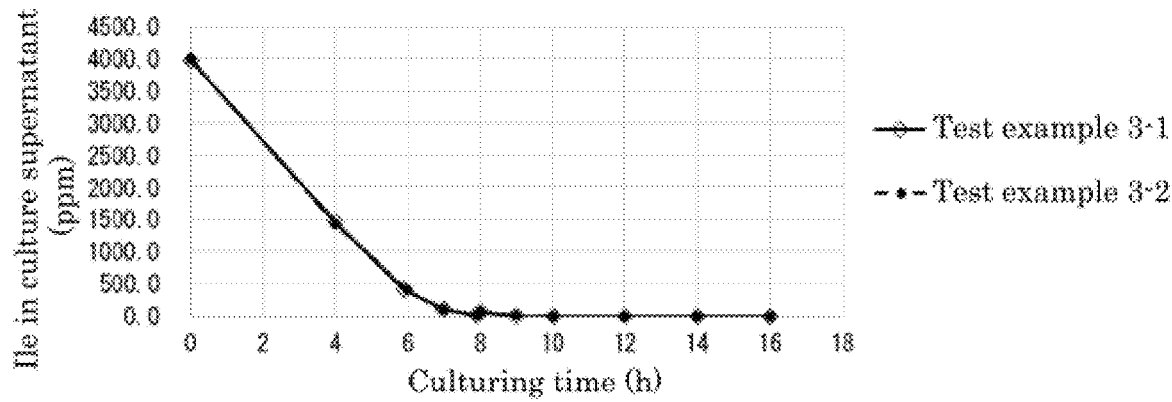
FIG. 3A is a graph plotting the measurements of isoleucine content in a culture supernatant during main culture in Test example 3.
Figure 3B:
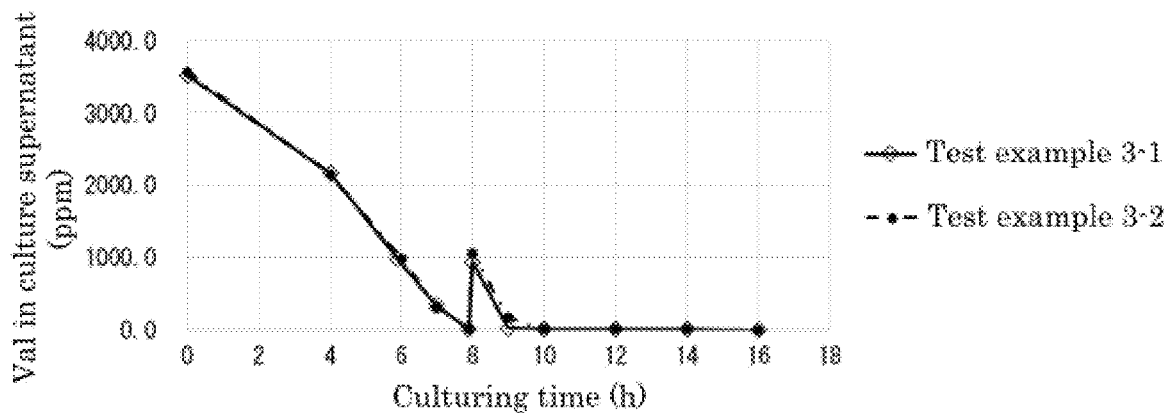
FIG. 3B is a graph plotting the measurements of valine content in a culture supernatant during main culture in Test example 3.

The results are plotted in FIG. 3A (isoleucine) and FIG. 3B (valine). In FIGS. 3A and 3B, "◇, solid line" plots the results of Test example 3-1, and "●, dashed line" plots the results of Test example 3-2.

—Measurement of Dry Cell Weight of Yeast—

The dry cell weight of yeast at the start of the main culture, and after two hours, four hours, six hours, seven hours, eight hours, nine hours, ten hours, 11 hours, 12 hours, 13 hours, 14 hours, 16 hours, and 18 hours from the start of the main culture was measured in the same manner as in Test example 1.

Figure 3C:
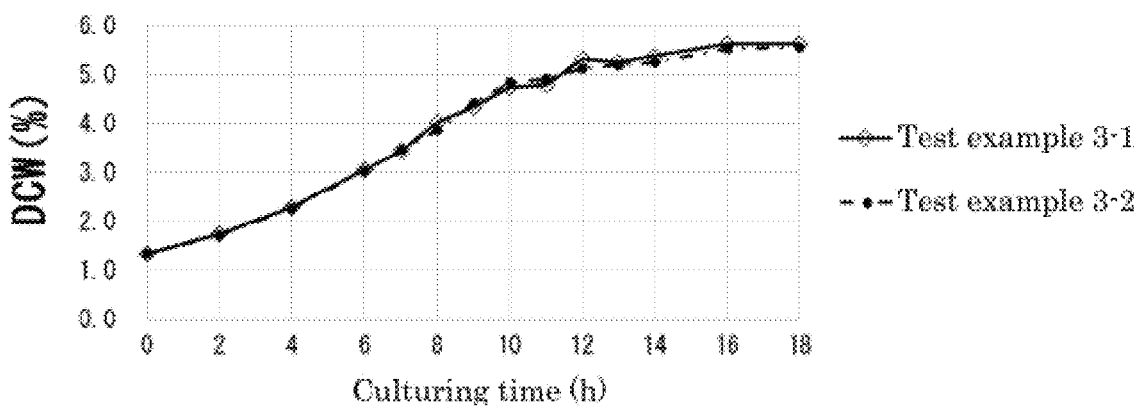
FIG. 3C is a graph plotting the measurements of dry cell weight of yeast during main culture in Test example 3.

The results are plotted in FIG. 3C. In FIG. 3C, "◇, solid line" plots the results of Test example 3-1, and "●, dashed line" plots the results of Test example 3-2.

—Measurement of, for Example, Rich Taste Imparting Substances—

The yeast was collected after six hours, seven hours, eight hours, nine hours, ten hours, 11 hours, 12 hours, 13 hours, 14 hours, and 16 hours from the start of the main culture, and the contents (amounts per dry cell weight of yeast) of γ-Glu-Abu and γ-Glu-Abu-Gly, which were the rich taste imparting substances, and of Abu, which was the precursor of γ-Glu-Abu and γ-Glu-Abu-Gly, in the yeast were measured in the same manner as the method described in <Selection-2> in (Preparation example 1).

Figure 3D:
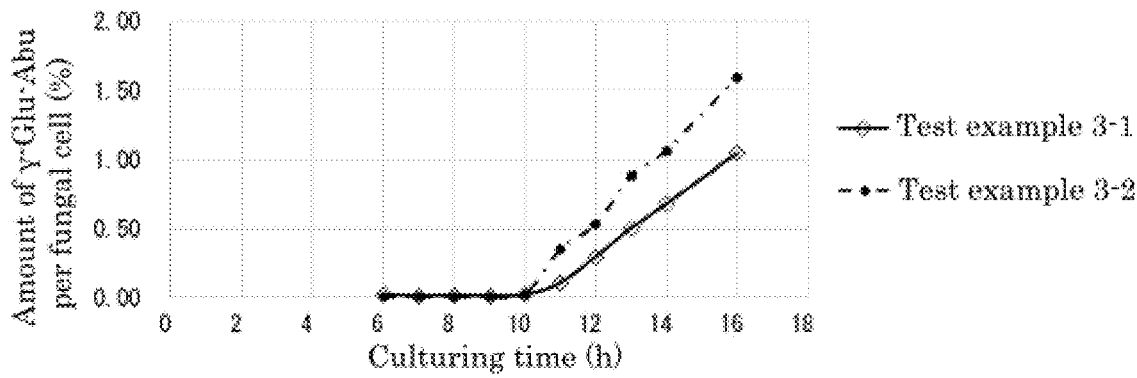
FIG. 3D is a graph plotting the measurements of γ-Glu-Abu amount per dry cell weight of yeast during main culture in Test example 3.
Figure 3E:
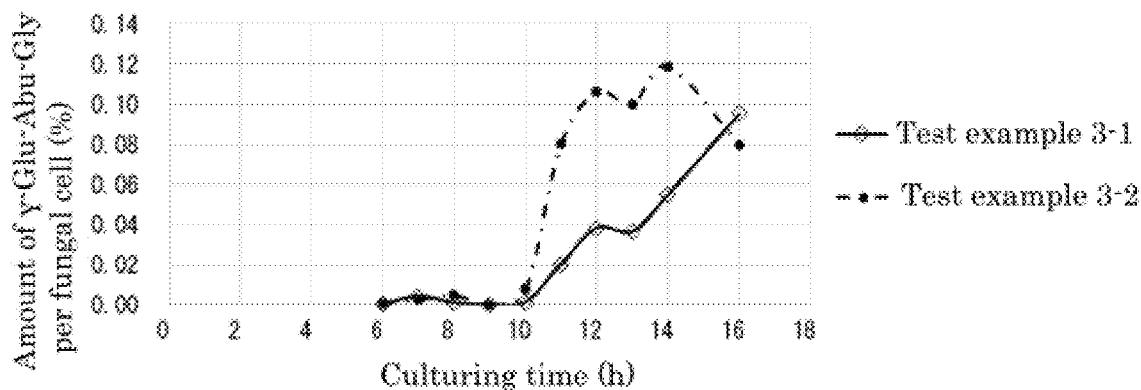
FIG. 3E is a graph plotting the measurements of γ-Glu-Abu-Gly amount per dry cell weight of yeast during main culture in Test example 3.
Figure 3F:
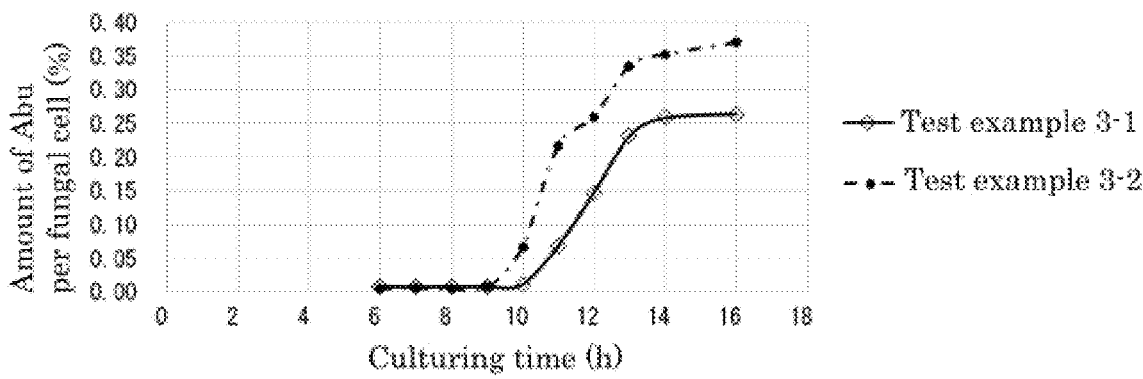
FIG. 3F is a graph plotting the measurements of Abu amount per dry cell weight of yeast during main culture in Test example 3.

The results are plotted in FIG. 3D (γ-Glu-Abu), FIG. 3E (γ-Glu-Abu-Gly), and FIG. 3F (Abu). In FIGS. 3D to 3F, "◇, solid line" plots the results of Test example 3-1, and "●, dashed line" plots the results of Test example 3-2.

As plotted in FIGS. 3A to 3F, addition of threonine when adding valine during the main culture resulted in production of the rich taste imparting substances and the precursor thereof in greater amounts.

Test Example 4

A yeast extract was prepared in the manner described below, using a culture obtained by performing culturing in the same manner as in Test example 3-2 except that the culturing time of the main culture among the culturing conditions of Test example 3-2 was changed to 12 hours after addition of valine and threonine (i.e., a culture after 20 hours from the start of the main culture).

First, the culture was centrifuged to collect the yeast contained in the culture as a precipitate, and the yeast was washed with distilled water. Subsequently, distilled water in a proper amount was added to the yeast to adjust the fungal cell concentration to from 10% by weight through 15% by weight, to produce a yeast suspension. The yeast suspension was heated at 85° C. for 70 seconds, then rapidly cooled, and centrifuged, to collect the extract content. The collected extract content was dried, to produce a yeast extract.

<<Measurement>>

—Measurement of Rich Taste Imparting Substances—

The contents (amounts per dry weight of yeast extract) of γ-Glu-Abu and γ-Glu-Abu-Gly, which were the rich taste imparting substances in the yeast extract, were measured in the same manner as the method described in <Selection-2> in (Preparation example 1). As a result, the content of γ-Glu-Abu per dry weight of yeast extract was 9.40%, and the content of γ-Glu-Abu-Gly per dry weight of yeast extract was 1.13%. Accordingly, it was confirmed that the method of the present invention was able to produce a yeast extract in which the contents of the rich taste imparting substances per dry weight of yeast extract were greater than 10%.

Test Example 5

The K16-2 strains obtained in Preparation example 1 were subjected to preculture and main culture in the same manners as in the case in which the jar was used in <Selection-3> in Preparation example 1, except that the cultures were performed under the conditions described in <Test example 5-1> to <Text example 5-5> below.

Test Example 5-1

The main culture was continued without addition of valine and threonine (control).

Test Example 5-2

During the main culture, valine (500 ppm) (1.5% per dry cell weight of yeast) was added to the culture medium after 7.5 hours passed from the start of the main culture, and the main culture was continued.

The isoleucine content in the culture supernatant immediately before the addition of valine was 12.3 ppm (0.00123% by mass), and the valine content therein was 16.0 ppm (0.00160% by mass).

Test Example 5-3

During the main culture, valine (1,000 ppm) (3.0% per dry cell weight of yeast) was added to the culture medium after 7.5 hours passed from the start of the main culture, and the main culture was continued.

The isoleucine content in the culture supernatant immediately before the addition of valine was 0 ppm, and the valine content therein was 0 ppm.

Test Example 5-4

During the main culture, valine (1,500 ppm) (4.5% per dry cell weight of yeast) was added to the culture medium after 7.5 hours passed from the start of the main culture, and the main culture was continued.

The isoleucine content in the culture supernatant immediately before the addition of valine was 0 ppm, and the valine content therein was 0 ppm.

Test Example 5-5

During the main culture, valine (1,000 ppm) (3.0% per dry cell weight of yeast) was and threonine (1,000 ppm) (3.0% per dry cell weight of yeast) were added to the culture medium after 7.5 hours passed from the start of the main culture, and the main culture was continued.

The isoleucine content in the culture supernatant immediately before the addition of valine and threonine was 0 ppm, and the valine content therein was 7.5 ppm (0.00075% by mass).

<Measurement>

—Measurement of Isoleucine and Valine Contents in Culture Supernatant—

The isoleucine and valine contents in the culture supernatant at the start of the main culture, and after two hours, four hours, six hours, 7.5 hours, eight hours, nine hours, ten hours, 12 hours, and 14 hours from the start of the main culture were measured in the same manner as in Test example 1.

Figure 4A:
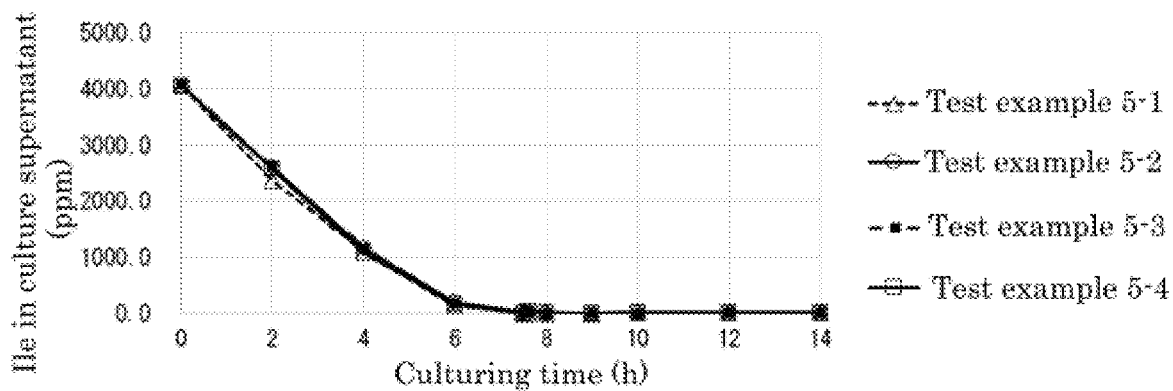
FIG. 4A is a graph-1 plotting the measurements of isoleucine content in a culture supernatant during main culture in Test example 5.
Figure 4B:
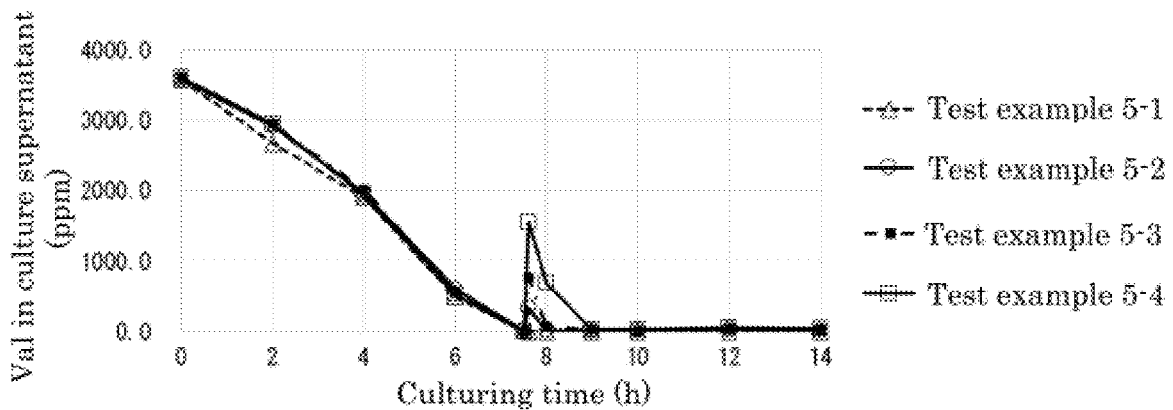
FIG. 4B is a graph-1 plotting the measurements of valine content in a culture supernatant during main culture in Test example 5.
Figure 4C:
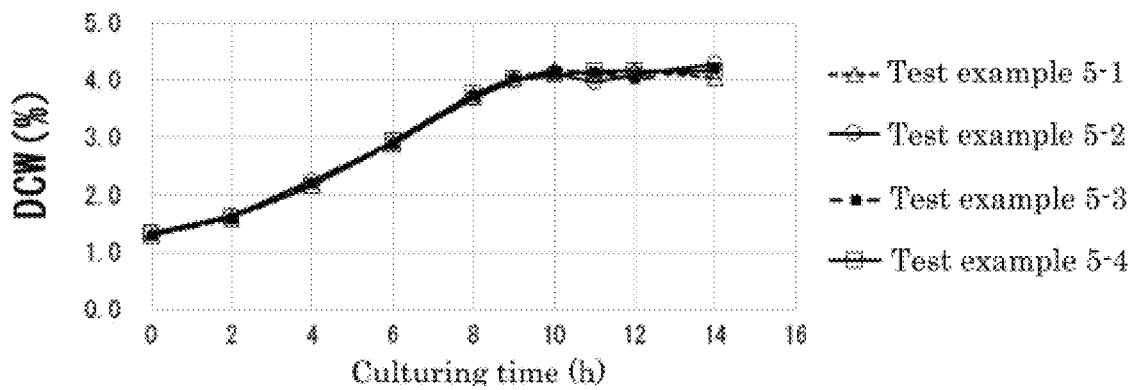
FIG. 4C is a graph-1 plotting the measurements of dry cell weight of yeast during main culture in Test example 5.
Figure 4D:
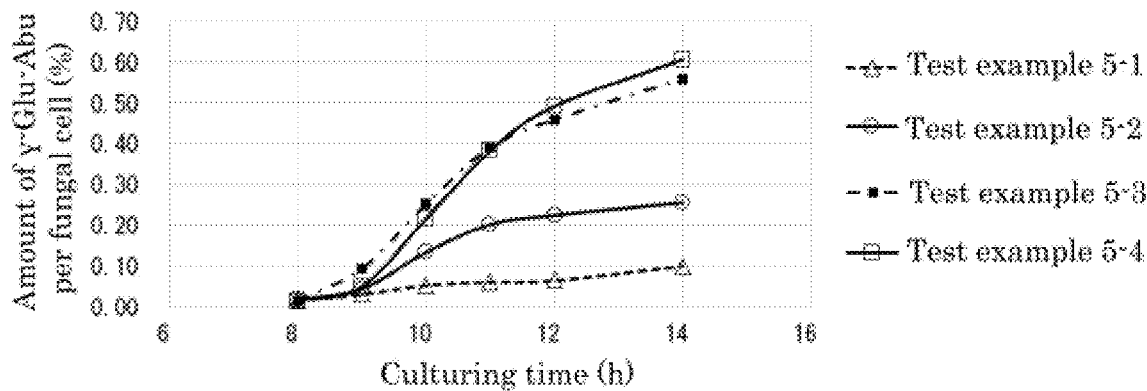
FIG. 4D is a graph-1 plotting the measurements of γ-Glu-Abu amount per dry cell weight of yeast during main culture in Test example 5.
Figure 4E:
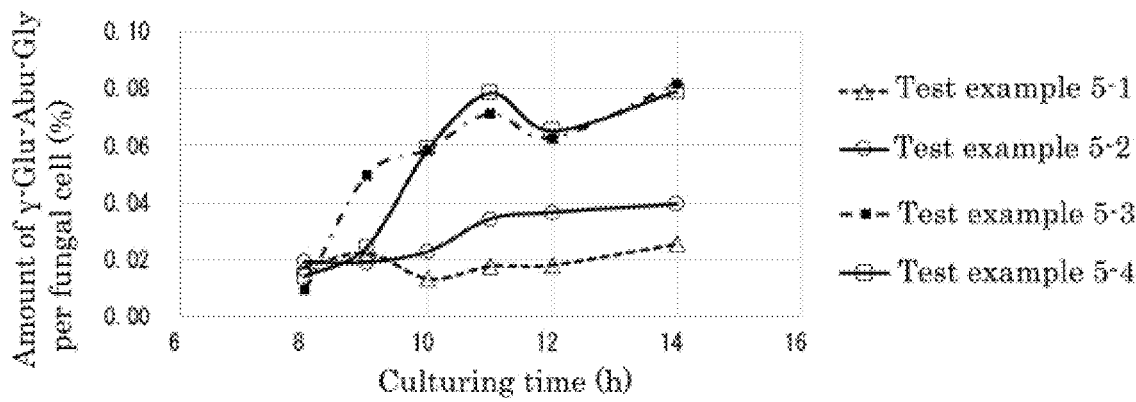
FIG. 4E is a graph-1 plotting the measurements of γ-Glu-Abu-Gly amount per dry cell weight of yeast during main culture in Test example 5.
Figure 4F:
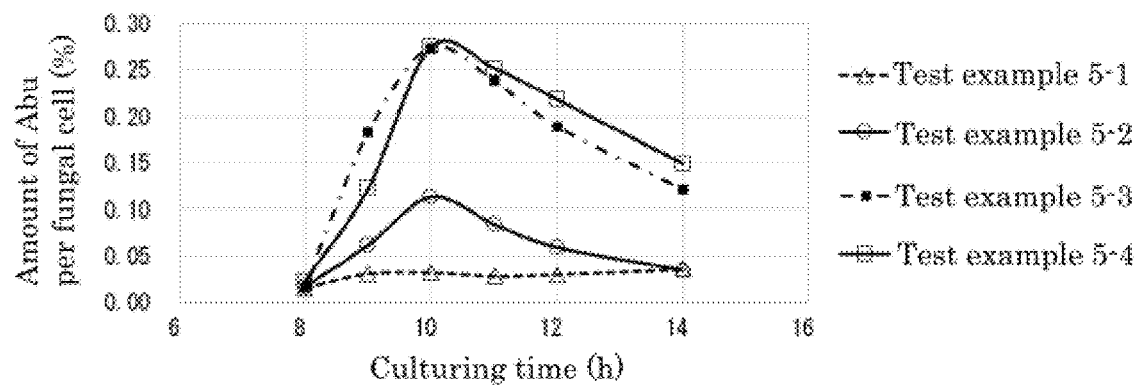
FIG. 4F is a graph-1 plotting the measurements of Abu amount per dry cell weight of yeast during main culture in Test example 5.
Figure 4G:
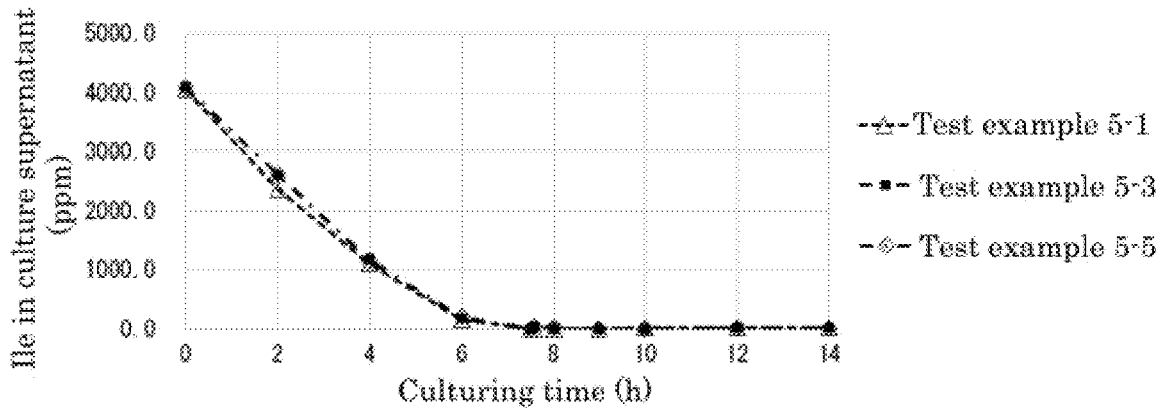
FIG. 4G is a graph-2 plotting the measurements of isoleucine content in a culture supernatant during main culture in Test example 5.
Figure 4H:
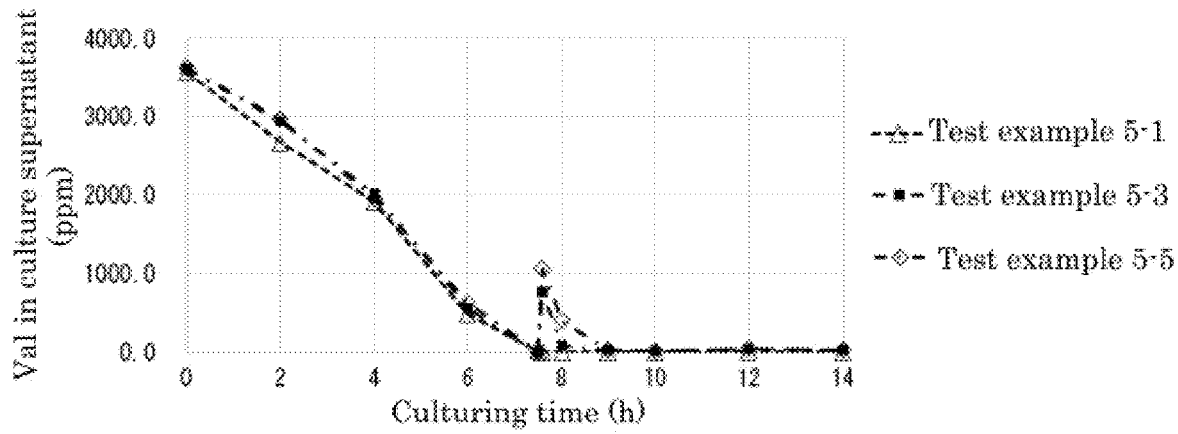
FIG. 4H is a graph-2 plotting the measurements of valine content in a culture supernatant during main culture in Test example 5.

The results are plotted in FIGS. 4A and 4G (isoleucine) and FIGS. 4B and 4H (valine). In FIGS. 4A, 4B, 4G, and 4H, "Δ, dotted line" plots the results of Test example 5-1, "○, solid line" plots the results of Test example 5-2, "■, dashed line" plots the results of Test example 5-3, "□, solid line"

plots the results of Test example 5-4, and "◇, dashed line" plots the results of Test example 5-5.

—Measurement of Dry Cell Weight of Yeast—

The dry cell weight of yeast at the start of the main culture, and after two hours, four hours, six hours, eight hours, nine hours, ten hours, 11 hours, 12 hours, and 14 hours from the start of the main culture was measured in the same manner as in Test example 1.

Figure 4I:
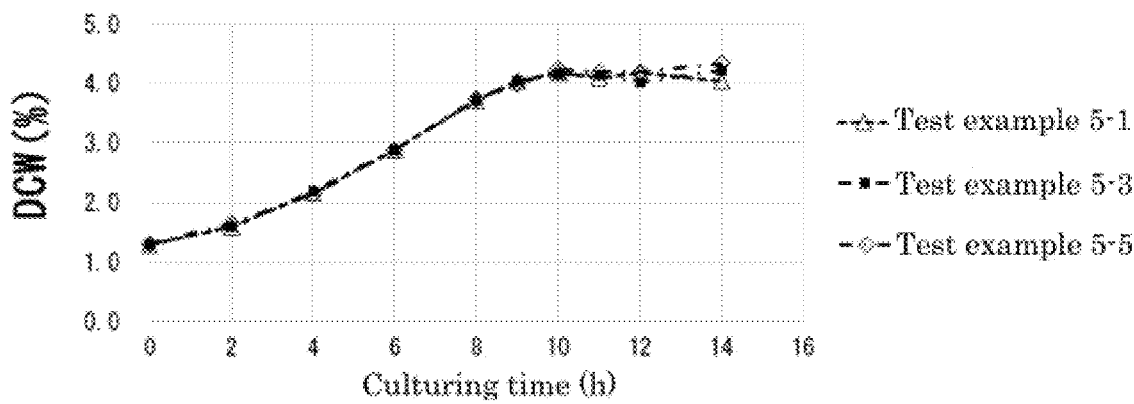
FIG. 4I is a graph-2 plotting the measurements of dry cell weight of yeast during main culture in Test example 5.

The results are plotted in FIGS. 4C and 4I. In FIGS. 4C and 4I, "▲, dotted line" plots the results of Test example 5-1, "○, solid line" plots the results of Test example 5-2, "■, dashed line" plots the results of Test example 5-3, "□, solid line" plots the results of Test example 5-4, and "◇, dashed line" plots the results of Test example 5-5.

—Measurement of, for Example, Rich Taste Imparting Substances—

The yeast was collected after eight hours, nine hours, ten hours, 11 hours, 12 hours, and 14 hours from the start of the main culture, and the contents (amounts per dry cell weight of yeast) of γ-Glu-Abu and γ-Glu-Abu-Gly, which were the rich taste imparting substances, and of Abu, which was the precursor of γ-Glu-Abu and γ-Glu-Abu-Gly, in the yeast were measured in the same manner as the method described in <Selection-2> in (Preparation example 1).

Figure 4J:
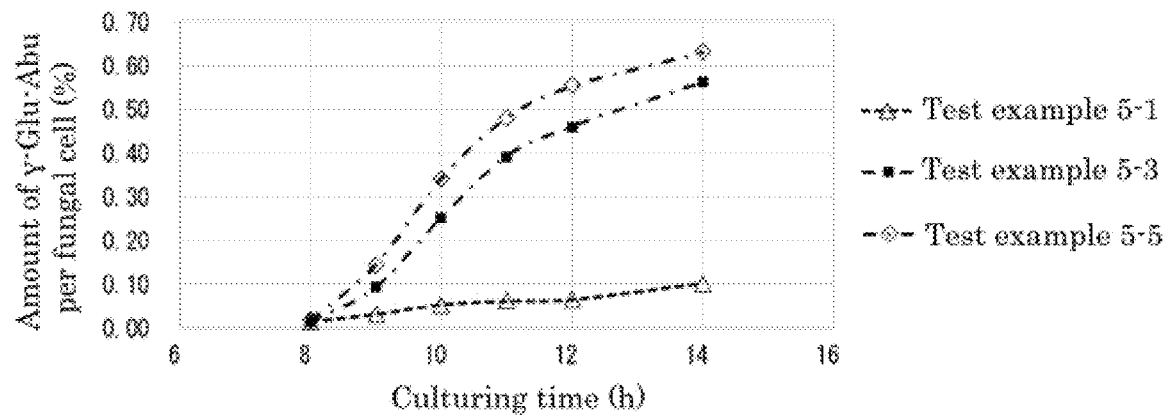
FIG. 4J is a graph-2 plotting the measurements of γ-Glu-Abu amount per dry cell weight of yeast during main culture in Test example 5.
Figure 4K:
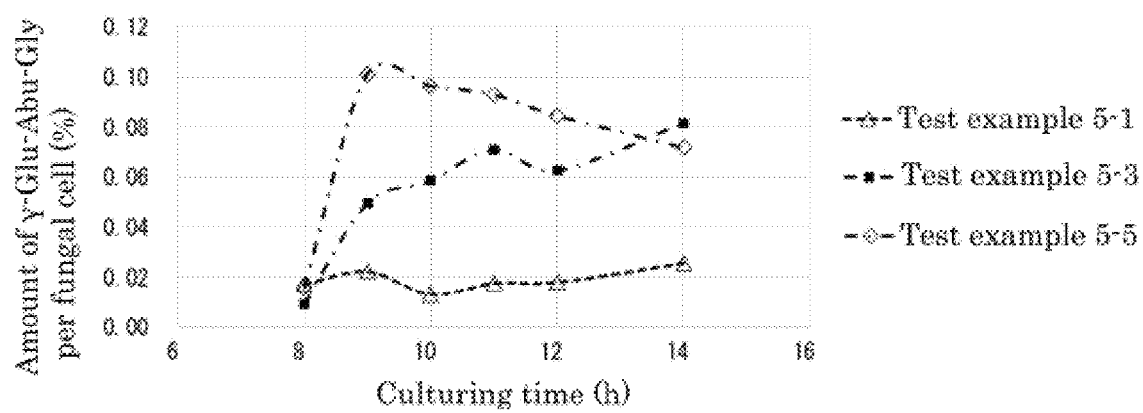
FIG. 4K is a graph-2 plotting the measurements of γ-Glu-Abu-Gly amount per dry cell weight of yeast during main culture in Test example 5.
Figure 4L:
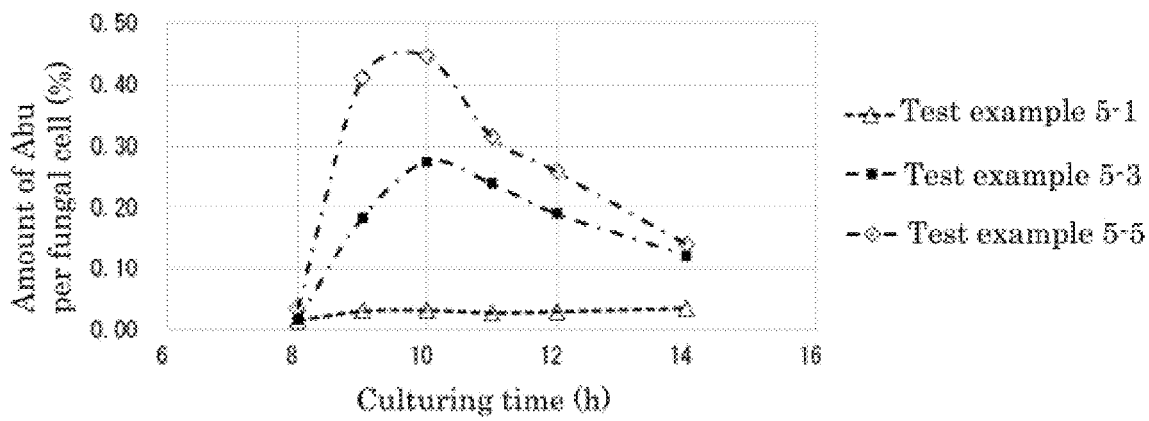
FIG. 4L is a graph-2 plotting the measurements of Abu amount per dry cell weight of yeast during main culture in Test example 5.

The results are plotted in FIGS. 4D and 4J (γ-Glu-Abu), FIGS. 4E and 4K (γ-Glu-Abu-Gly), and FIGS. 4F and 4L (Abu). In FIGS. 4D, 4E, 4F, 4J, 4K, and 4L, "△, dotted line" plots the results of Test example 5-1, "○, solid line" plots the results of Test example 5-2, "■, dashed line" plots the results of Test example 5-3, "□, solid line" plots the results of Test example 5-4, and "◇, dashed line" plots the results of Test example 5-5.

As plotted in FIGS. 4A to 4L, increase in the amount of valine added during the main culture resulted in production of the rich taste imparting substances and the precursor thereof in greater amounts. It was confirmed also in the present Test example that addition of threonine when adding valine resulted in production of the rich taste imparting substances and the precursor thereof in greater amounts.

Aspects of the present invention are, for example, as follows.

<1> A method for producing a rich taste imparting substance-containing yeast, the method including:
   a yeast proliferating step of culturing a yeast that is modified to have a reduced acetolactate synthase activity in cells and has isoleucine and valine requirements in a culture medium containing isoleucine and valine, to proliferate the yeast; and
   a rich taste imparting substance producing step of culturing the yeast with addition of valine to the culture medium when an isoleucine content in the culture medium is less than 0.2% by mass, to produce a rich taste imparting substance,
   wherein the rich taste imparting substance is at least one of γ-Glu-Abu and γ-Glu-Abu-Gly.

<2> The method for producing a rich taste imparting substance-containing yeast according to <1>,
   wherein the yeast is a yeast modified to have an enhanced ability to produce glutathione.

<3> The method for producing a rich taste imparting substance-containing yeast according to <1> or <2>,
   wherein in the rich taste imparting substance producing step, threonine is further added to the culture medium.

<4> The method for producing a rich taste imparting substance-containing yeast according to any one of <1> to <3>,
   wherein a content of the rich taste imparting substance in the rich taste imparting substance-containing yeast is 0.3% or greater per dry cell weight of yeast.

<5> A method for producing a rich taste imparting substance-containing yeast extract, the method including preparing a yeast extract from the rich taste imparting substance-containing yeast obtained by the method for producing a rich taste imparting substance-containing yeast according to any one of <1> to <4>.

<6> The method for producing a rich taste imparting substance-containing yeast extract according to <5>,
   wherein a content of the rich taste imparting substance in the rich taste imparting substance-containing yeast extract is greater than 1% per dry weight of yeast extract.

The invention claimed is:

1. A method for producing a-yeast containing either or both substances γ-Glu-Abu and γ-Glu-Abu-Gly, the method comprising:
   culturing a yeast that is modified to have a reduced acetolactate synthase activity in cells and has isoleucine and valine requirements in a culture medium containing isoleucine and valine, to proliferate the yeast; and
   culturing the yeast with addition of valine to the culture medium when an isoleucine content in the culture medium is 0.05% by mass or less, to produce either or both of the substance γ-Glu-Abu and γ-Glu-Abu-Gly.

2. The method for producing a yeast containing either or both substances γ-Glu-Abu and γ-Glu-Abu-Gly according to claim 1,
   wherein the yeast is a yeast modified to have an enhanced ability to produce glutathione.

3. The method for producing a yeast containing either or both substances γ-Glu-Abu and γ-Glu-Abu-Gly according to claim 1,
   wherein in the culturing the yeast with addition of valine to produce either or both of the substances γ-Glu-Abu and γ-Glu-Abu-Gly, threonine is further added to the culture medium.

4. The method for producing a yeast containing either or both substances γ-Glu-Abu and γ-Glu-Abu-Gly according to claim 1,
   wherein a content of either or both of the substances γ-Glu-Abu and γ-Glu-Abu-Gly in the yeast containing either or both of the substances γ-Glu-Abu and γ-Glu-Abu-Gly is 0.3% or greater per dry cell weight of yeast.

5. A method for producing a yeast extract containing either or both of the substances γ-Glu-Abu and γ-Glu-Abu-Gly, the method comprising:
   preparing a yeast extract from a yeast containing either or both of the substances γ-Glu-Abu and γ-Glu-Abu-Gly, the yeast being obtained by a method for producing a yeast containing either or both of the substances γ-Glu-Abu and γ-Glu-Abu-Gly,
   wherein the method for producing a yeast containing either or both of the substances γ-Glu-Abu and γ-Glu-Abu-Gly comprises:
      culturing a yeast that is modified to have a reduced acetolactate synthase activity in cells and has isoleucine and valine requirements in a culture medium containing isoleucine and valine, to proliferate the yeast; and
      culturing the yeast with addition of valine to the culture medium when an isoleucine content in the culture medium is 0.05% by mass or less, to produce either or both of the substances γ-Glu-Abu and γ-Glu-Abu-Gly.

6. The method for producing a yeast extract containing either or both of the substances γ-Glu-Abu and γ-Glu-Abu-Gly according to claim 5,
wherein a content of either or both of the substances γ-Glu-Abu and γ-Glu-Abu-Gly in the yeast extract containing either or both of the substances γ-Glu-Abu and γ-Glu-Abu-Gly is greater than 1% per dry weight of yeast extract.

7. The method for producing a yeast containing either or both of the substances γ-Glu-Abu and γ-Glu-Abu-Gly according to claim 2,
wherein in the culturing the yeast with addition of valine to produce either or both of the substances γ-Glu-Abu and γ-Glu-Abu-Gly, threonine is further added to the culture medium.

8. The method for producing a yeast containing either or both of the substances γ-Glu-Abu and γ-Glu-Abu-Gly according to claim 2,
wherein a content of either or both of the substances γ-Glu-Abu and γ-Glu-Abu-Gly in the yeast containing either or both of the substances γ-Glu-Abu and γ-Glu-Abu-Gly is 0.3% or greater per dry cell weight of yeast.

9. The method for producing a yeast containing either or both of the substances γ-Glu-Abu and γ-Glu-Abu-Gly according to claim 3,
wherein a content of either or both of the substances γ-Glu-Abu and γ-Glu-Abu-Gly in the yeast containing either or both of the substances γ-Glu-Abu and γ-Glu-Abu-Gly is 0.3% or greater per dry cell weight of yeast.

10. The method for producing a yeast containing either or both of the substances γ-Glu-Abu and γ-Glu-Abu-Gly according to claim 7,
wherein a content of either or both of the substances γ-Glu-Abu and γ-Glu-Abu-Gly in the yeast containing either or both of the substances γ-Glu-Abu and γ-Glu-Abu-Gly is 0.3% or greater per dry cell weight of yeast.

11. The method for producing a yeast extract containing either or both of the substances γ-Glu-Abu and γ-Glu-Abu-Gly according to claim 5,
wherein the yeast is a yeast modified to have an enhanced ability to produce glutathione.

12. The method for producing a yeast extract containing either or both of the substances γ-Glu-Abu and γ-Glu-Abu-Gly according to claim 5,
wherein in the culturing the yeast with addition of valine to produce either or both of the substances γ-Glu-Abu and γ-Glu-Abu-Gly, threonine is further added to the culture medium.

13. The method for producing a yeast extract containing either or both of the substances γ-Glu-Abu and γ-Glu-Abu-Gly according to claim 5,
wherein a content of either or both of the substances γ-Glu-Abu and γ-Glu-Abu-Gly in the yeast containing either or both of the substances γ-Glu-Abu and γ-Glu-Abu-Gly is 0.3% or greater per dry cell weight of yeast.

14. The method for producing a yeast extract containing either or both of the substances γ-Glu-Abu and γ-Glu-Abu-Gly according to claim 6,
wherein the yeast is a yeast modified to have an enhanced ability to produce glutathione.

15. The method for producing a yeast extract containing either or both of the substances γ-Glu-Abu and γ-Glu-Abu-Gly according to claim 6,
wherein in the culturing the yeast with addition of valine, threonine is further added to the culture medium.

16. The method for producing a yeast extract containing either or both of the substances γ-Glu-Abu and γ-Glu-Abu-Gly according to claim 6,
wherein a content of either or both of the substances γ-Glu-Abu and γ-Glu-Abu-Gly in the yeast containing either or both of the substances γ-Glu-Abu and γ-Glu-Abu-Gly is 0.3% or greater per dry cell weight of yeast.

\* \* \* \* \*